United States Patent
Purvis et al.

(10) Patent No.: US 8,404,096 B2
(45) Date of Patent: Mar. 26, 2013

(54) METHODS FOR PRODUCING HIGHLY SENSITIVE POTENTIOMETRIC SENSORS

(75) Inventors: Duncan Ross Purvis, Royston (GB); Olga Leonardova, Royston (GB); Dmitri Alexandrovich Farmakovski, Moscow (RU); Vladimir Rurikovich Tcherkassov, Moscow (RU)

(73) Assignee: Sensortec Limited (GB)

( * ) Notice: Subject to any disclaimer, the term of this patent is extended or adjusted under 35 U.S.C. 154(b) by 3090 days.

(21) Appl. No.: 10/486,840

(22) PCT Filed: Aug. 23, 2002

(86) PCT No.: PCT/GB02/03894
§ 371 (c)(1), (2), (4) Date: Feb. 23, 2004

(87) PCT Pub. No.: WO03/019171
PCT Pub. Date: Mar. 6, 2003

(65) Prior Publication Data
US 2004/0182719 A1   Sep. 23, 2004

(30) Foreign Application Priority Data

Aug. 24, 2001  (GB) .................................. 0120674.7
Jan. 30, 2002  (GB) .................................. 0202151.7

(51) Int. Cl.
*C25B 3/10*   (2006.01)
*C25D 13/08*  (2006.01)
*C12Q 1/00*   (2006.01)
*G01N 27/26*  (2006.01)
*G01N 27/333* (2006.01)

(52) U.S. Cl. ........ 205/106; 205/107; 205/317; 205/341; 205/414; 205/787.5; 205/792

(58) Field of Classification Search .................. 205/106, 205/317
See application file for complete search history.

(56) References Cited

U.S. PATENT DOCUMENTS

| | | | | |
|---|---|---|---|---|
| 4,235,942 A | * | 11/1980 | Heller et al. | 426/656 |
| 4,582,575 A | * | 4/1986 | Warren et al. | 205/55 |
| 4,609,437 A | * | 9/1986 | Kruishoop et al. | 205/138 |
| 5,233,000 A | * | 8/1993 | Yodice | 526/258 |
| 5,403,451 A | * | 4/1995 | Riviello et al. | 205/777.5 |
| 6,288,890 B1 | * | 9/2001 | Saito et al. | 361/523 |
| 6,655,010 B1 | * | 12/2003 | Hatfield et al. | 29/610.1 |

FOREIGN PATENT DOCUMENTS

| | | |
|---|---|---|
| WO | 89 11649 A | 11/1989 |
| WO | 96 02001 A | 1/1996 |
| WO | 98 37409 A | 8/1998 |
| WO | 00 11473 A | 3/2000 |

OTHER PUBLICATIONS

PubChem Public Chemical Database, http://www.chemindustry.com/apps/chemicals, entry for sodium dodecyl sulfate, 2008.*

* cited by examiner

*Primary Examiner* — Patrick Ryan
*Assistant Examiner* — William Leader
(74) *Attorney, Agent, or Firm* — Bacon & Thomas, PLLC

(57) ABSTRACT

The invention relates to methods of preparation of highly sensitive potentiometric sensors with an electroconductive polymer film as a sensing element.

22 Claims, 8 Drawing Sheets

US 8,404,096 B2

METHODS FOR PRODUCING HIGHLY SENSITIVE POTENTIOMETRIC SENSORS

FIELD OF THE INVENTION

The invention relates to methods of preparation of highly sensitive potentiometric sensors with an electroconductive polymer film as a sensing element. The invention is applicable to the fields of medicine, biotechnology, agriculture, ecology as well as to environment monitoring and food quality assurance, particularly to laboratory testing of biological and environmental fluids performed for the purpose of clinical diagnostics, proteomics, cell analysis, environmental and manufacturing monitoring and research.

BACKGROUND TO THE INVENTION

The use of sensors with an electroconductive polymer film as a sensing element is one of the most promising and attractive methods of quantitative electrochemical analysis [1]. To date, a number of electrochemical sensors based on electroconductive polymers have been described. They are distinguished by the principle of the measurement (amperometric, voltamperometric, chemoresistive, potentiometric) as well as by the method of receiving the analytical signal (direct and non-direct sensors).

The amperometric signal is received by applying to a sensor a constant voltage from external source and measuring a level of current defined by chemical and/or biochemical reaction taking place within the sensor [2]. Voltamperometric and chemoresistive sensors work similarly in principle but with the difference that the applied voltage is not constant, being changed according to established parameters for a particular method [2, 3].

As a rule amperometric and voltamperometric methods require expensive equipment including an amperometer, external source of voltage or potentiostat, a counter electrode and a reference electrode [2].

Potentiometric devices derive their responses from the change in redox composition of the electroconductive polymer because of the chemical and/or biological reaction, which accompanies the changes in the steady state potential of the potentiometric sensor [2, 4, 5]. The authors of the present invention observe that potentiometric sensors have a number of advantages over amperometric and voltamperometric sensors. One of them is that potentiometric methods do not require sophisticated equipment. A potentiometric device usually comprises a sensor itself, a reference electrode and a high impedance voltmeter [2, 6]. Secondly the signal does not depend on a surface area or a shape of a sensor [2]. Thirdly with a potentiometric method of measurement the problems associated with diffusion processes within the electrochemical cell and resulting in complicated constructions of electrodes (e.g. rotating disc electrodes) for amperometric and voltamperometric methods of measurement, do not play a significant role [2, 4].

The use of potentiometric measurement can be as simple as pH measurement, and the potentiometric device can be similar to commercial pH or ion-selective electrodes.

All electrochemical sensors can be divided into two types, direct and indirect sensors.

A direct electrochemical sensor generates the signal immediately at the moment of interaction between an analyte and receptors immobilised within or adsorbed onto the sensor. Examples of direct sensors are enzyme amperometric sensors [2, 7, 8], ion-selective potentiometric sensors [9, 10] and potentiometric immunosensors [11, 12, 13]. As a rule the contact with an analyte and the measurement procedure are performed simultaneously.

An indirect electrochemical sensor generates a signal due to the presence of additional agents specific to an analyte carrying electrochemically active labels. Examples of the sensors belonging to indirect group are amperometric and potentiometric enzyme sensors [2], potentiometric sensors sensitive to a change in surface potential [14, 15] as well as voltamperometric and chemoresistive sensors [16, 17, 18]. The contact between the sensor and an analyte and the measurement procedure are separated in time and space.

The voltamperometric sensors can be described as intermediate between direct and indirect sensors. In this case there are no labelled agents in the system but the incubation and measurement steps are separated in time and space and/or solute.

The most critical step in the manufacture of a highly sensitive potentiometric sensor, having a conductive polymer layer as a sensing element, is the formation of the polymer film on the conductive support. The support itself is usually a noble metal, carbon or semi-conductive material [19]. Electrochemical synthesis allows production of conductive polymer films with defined chemical, electrochemical and mechanical properties [19].

The components of the polymerisation process include monomer(s), a polar solvent and at least two electrodes (auxiliary and working) [19]. A supporting electrolyte is usually included in the polymerisation solution to increase conductivity of the solution and for doping the polymer at the polymerisation step [19]. There are three main types of electrochemical synthesis: galvanostatic, potentiostatic and potentiodynamic [19].

In the galvanostatic method a constant current from an external source is applied for period of time between working and auxiliary electrodes immersed in the polymerisation solution. The reference electrode may be used to control the electrochemical potential of the working electrode [19, 20, 21].

In the potentiostatic method usually three electrodes are required. The current between the working and auxiliary electrodes is controlled by an amperometer set at a constant voltage from an external source (which is in its turn controlled by the reference electrode) applied between the working electrode and auxiliary electrode for a certain period of time [19, 20, 21].

In the potentiodynamic method the voltage applied between the working and auxiliary electrodes is not constant, but is changing according to established procedures [19, 20, 21].

The most important property for potentiometric enzyme- or immunosensors is their redox sensitivity [4], because most of the enzyme reactions are redox processes accompanied by changing redox state of reactants. The redox sensitivity of polymer-based sensors is completely defined by redox properties of the polymer film [22], which in their turn are defined by the conditions and parameters of the polymerisation process.

A large number of publications are dedicated to research of redox properties of electroconductive polymers, e.g. polypyrrole [5, 22-27]. In a number of these studies [22-23, 26] it was shown that two main mechanisms are employed in the formation of the potentiometric signal. The irreversible change in the intrinsic redox state of the electroconductive polymer is a consequence of the interaction between the polymer layer and electrochemical active species and is referred to as a "corrosive type" of formation potentiometric response. This process is always accompanied by an ionic exchange between the polymer and surrounding solution. Another mechanism is based on an electron exchange between the redox couples on the polymer surface via the polymer film. The intrinsic redox state of the polymer does not change in this process, and an ionic exchange between polymer and solution does not take place. In this case the electroconductive polymer behaves as a metallic potentiometric electrode and its behaviour can be described by the Frumkin theory of electronic equilibrium [22, 28]. This is "metallic type" potentiometric response, and it is reversible. In reality both mechanisms act simultaneously but one of them can be predominant [22-23, 26, 27]. The "metallic type" is favoured for potentiometric redox sensors because it provides the quicker and stronger response [26]. It is possible to change the properties of the polymer film at the polymerisation step making the "metallic" mechanism predominant [22-23, 26].

Previously, the nature of a supporting electrolyte, and accordingly the nature of a dopant ion, were considered the only factors responsible for metallic properties of the polymer film [22-27, 29]. It was shown that the immobile anions embedded within the polymer film do not participate in ion exchange reactions, providing stability of intrinsic redox state [23, 26]. The examples of such electrolytes are dodecylsulphate [23], various dyes, e.g. indigo carmine and methylene blue [30, 31]. However, in all cited publications the concentration of dopant ions in polymerisation solution is not considered as a factor responsible for imparting the metallic properties to the polymer.

The authors of the present invention consider the concentration of the monomer as well as the concentration of supporting electrolyte in the solution for the electrochemical polymerisation as the most important factors for redox properties, and accordingly for redox sensitivity of the polymer. It is known that the concentration of the monomer can also influence the conductivity of polymer [19]. According to the data by the authors of the present invention, the best redox sensitivity can be reached using the polymerisation solution with much lower concentrations of monomer (<0.05M) than commonly used (0.05-0.5M). The authors of the present invention found that the ratio between the concentration of a monomer and supporting electrolyte is a key factor particularly responsible for redox properties and thickness of a polymer film. The ratio between monomer(s) and supporting electrolyte(s) as well as their concentrations had not previously been considered as factors responsible for redox properties of polymer film prior to the studies carried out by the present inventors.

Despite the fact that there are a substantial number of methods for electrochemical synthesis of the electroconductive polymer described in the literature, none of them provide the conditions and parameters for production of highly sensitive sensors suitable for potentiometric detection of biomolecules in low concentration.

Some examples of the prior art methods of electrochemical synthesis are given below.

Potentiostatic methods for preparation of electrochemical polypyrrole-based sensors from aqueous solutions in the presence of a supporting electrolyte are described in [39, 42, 43, 44 and 45].

Taniguchi et al [33] described the method for growing polypyrrole film from organic solvents in the presence of a supporting electrolyte using galvanostatic regime. The generated polymer films were used for the preparation of a direct potentiometric immunosensor. The main disadvantage of this method is that the sensitivity of the sensors produced by this method is poor (mg/ml of IgG). Another disadvantage is that the organic solvents used in such a method are highly toxic.

Other galvanostatic methods where water is used as a solvent are described in [13, 16, 17, 34, 35, 36, 37, 38, 39, 40, 41].

A potentiodynamic method of electrochemical polymerisation for synthesis of electroconductive polymers from aqueous solutions in the presence of a supporting electrolyte for preparation of electrochemical sensors has been described [9, 10, 27, 46, 47, 48, 49].

Most of the sensors produced by the methods described in the articles mentioned above were not intended to use for potentiometric measurement, but for other types of electrochemical measurement or entrapment. All of them are unsuitable for potentiometric assays requiring high analytical sensitivity, precision and stability. The methods cannot be developed directly to the method described in the present invention to provide the required properties of the sensors. The measuring procedures are always more complicated and takes longer than the one which is described in this invention.

The authors of the present invention have also described the potentiodynamic method of preparations of potentiometric polypyrrole-based sensors [50, 51].

Despite the possibility to use polymerisation solutions with low concentrations of monomer(s) in the potentiodynamic and galvanostatic regimes [19], most of the cited publications describe use of concentrations of 0.05M and higher. As it has been stressed by the authors of the present invention, polymer films grown from concentrated monomer solutions do not have high redox sensitivity and therefore cannot be used as a highly sensitive element of the polymer-based potentiometric sensor.

Low concentrations of monomer were mentioned in only one single study [48], but the authors used high concentrations of the supporting electrolytes (0.5M) and supporting electrolytes with highly mobile anions ($KCl$, $KNO_3$, $NaClO_4$, $Na_2HPO_4$), which are actively interactive in ionic exchange between polymer and surrounding solution. The potentiometric response of such sensors belongs mainly to the corrosion-type mechanism. This type of sensor is not sensitive enough for measurement of biological redox reactions, where clinically or environmentally relevant concentrations of analyte may routinely occur in the range of nanomoles, femtomoles or attomoles. Other studies also used highly mobile anions as dopant ions, resulting in sensors, which exhibit low sensitivity. The work of Hulanicki et al [27], where the authors doped polymer with $Cl^-$, can be given as an example. In this case the sensors demonstrated redox sensitivity only in presence of very high concentrations of redox couples (about 0.5M).

Other studies [9, 49, 51] used a suitable dopant ion-sodium dodecylsulphate, but high concentrations of polymer (0.05-0.3M), which is again not suitable for preparation of highly sensitive potentiometric redox sensors.

The present inventors have defined the main factors, which, in combination, are responsible for the redox properties of the polymer film and as a consequence are able to produce polymer-based potentiometric sensors with higher sensitivity than those described in the prior art. These factors are the concentration of a monomer(s); nature and concentration of the supporting electrolyte; parameters of the polymerisation process; ratio between the concentrations of monomer and supporting electrolyte. The prior studies relate to only one or two parameters or conditions and not their synergistic influences or interferences. The authors of the present invention have found that a highly sensitive polymer film can be produced by combining all of the factors mentioned above.

SUMMARY OF THE INVENTION

The present invention relates to the production of highly sensitive reproducible and long-term stable polymer-based potentiometric sensors.

In a first aspect, the invention relates to a method of electrochemical synthesis of a polymer film with high redox sensitivity, which can serve as a sensing element of highly sensitive potentiometric chemical, enzyme- and immunosensors. There are three main types of electrochemical synthesis: galvanostatic, potentiostatic and potentiodynamic [19]. All of these can be used either alone or in combination to electrochemically grow the polypyrrole layer.

Thus, the invention provides a method for producing highly sensitive potentiometric sensors by coating of electrically conductive electrodes with an electroconductive polymer, which method comprises the steps of:

(a) preparing an aqueous solution for electrochemical polymerisation comprising monomeric units of the electroconductive polymer at a concentration in the range of from 0.002 to 0.05M; and a supporting electrolyte, which also serves as a doping agent, at a concentration in the range of from 0.0001 to 0.005M;

(b) assembling an electrochemical polymerisation cell comprising the solution for electrochemical polymerisation, an auxiliary electrode, one or more working electrodes to be coated with electroconductive polymer, and optionally a reference electrode; and (c) coating the working electrode(s) with a polymer film by the electrochemical synthesis of polymer from the electrochemical polymerisation solution using at least one of the following electrochemical regimes:

(i) applying a cyclic voltage in the range of from −0.2 to +2.0 V vs Ag/AgCl reference electrode between the working electrode(s) to be coated and the auxiliary electrode;

(ii) applying a constant current in the single or multiple current steps with given current density in a range of from 0.01 to 1 mA/cm$^2$ between working electrode(s) to be coated and auxiliary electrode for defined period of time such that final quantity of electricity passed through working electrode(s) will lie in a range of from 10 to 250 mC/cm$^2$;

(iii) applying a constant potential in a single or multiple potential steps at the range of from 0 to 3 V between working electrode(s) to be coated and a reference electrode for defined period of time such that final quantity of electricity passed through the working electrode(s) will lie in a range of from 10 to 250 mC/cm$^2$;

(iv) any other electrochemical regime, where all the solution concentrations and electrochemical parameters previously stated are adhered to.

The basis of this method is the research conducted by authors, from which the following conclusions can be drawn:

Redox sensitivity of polymer (e.g. polypyrrole)-based potentiometric sensors increases significantly (sharply), when the electrochemical synthesis is performed from the solutions with low concentration of monomers (e.g. pyrrole) (<0.05M).

The increase in redox sensitivity is observed for a range of monomer (e.g. pyrrole) concentrations in the range from 0.002-0.05M in the presence of a supporting electrolyte, which serves as a doping agent, for example sodium dodecylsulphate.

The ultimate increase of redox sensitivity is observed when the ratio between the molar concentrations of monomer (e.g. pyrrole) and supporting electrolyte is approximately 25:1 (although other ratios may be used within the scope of the invention) and either one or more of the following electrochemical polymerisation methods are used:

i) Potentiodynamic Regime: A cyclic voltage in the range −0.2−+2.0 V (vs Ag/AgCl reference electrode) is applied between the working electrode(s) (to be coated) and the reference electrode.

ii) Galvanostatic Regime: One or more (cascade) levels of current steps are applied in which the total charge passed during polymerisation is in the range from 10-250 mC/cm$^2$ iii) Potentiostatic Regime: One or more (cascade) levels of potential steps are applied between the working electrode and the reference electrode in which a total charge passed during polymerisation is in the range from 10-250 mC/cm$^2$.

The use of more than one level of current in galvanostatic regime and/or more than one level of applied potential in potentiostatic regime allows tight control of the properties of the sensor, and therefore production of sensors with better performance characteristics, e.g. more sensitive, than protocols using a single level of current or potential during electropolymerisation.

The concentrations of the monomer(s) and the supporting electrolyte(s), the ratio between them, and the applied polymerisation procedure synergistically influence redox sensitivity of polymer (e.g. polypyrrole)-based sensors.

The inventors' observations are unexpected because, as mentioned above, the relationship between redox sensitivity and such parameters as monomer(s) concentration, nature and concentration of supporting electrolyte and the ratio between them and parameters of the polymerisation procedure were not considered in previous publications. There is a strong correlation between redox sensitivity of the polymer film and the final analytical sensitivity of the sensor. A very important aspect of the present invention is that the observation that it is possible to regulate redox sensitivity by changing the composition of solution and parameters of the polymerisation process. It is possible to produce sensors for determination of some viral infections (e.g. HIV, HBsAg), where sensitivity at the level of femtomoles is required. Sometimes the range of interest for an analyte lies within higher concentrations, e.g. Digoxin (0.5-5 ng/ml) or IgE (20-1000 ng/ml).

The measuring range can be shifted to higher concentrations or extended by changing the set of parameters for the electrochemical polymerisation process or/and composition of the substrate system for further measurement procedure.

To summarise: analytical sensitivity and measuring range can be tailored for a particular analyte. This is achieved by the unique combination of the defined concentrations of monomers(s), supporting electrolyte in polymerisation solution and defined polymerisation regime in conjunction with the following treatment of the sensors.

This invention provides potentiodynamic, galvanostatic and potentiostatic methods for producing highly sensitive polymer-coated (e.g. polypyrrole-coated) potentiometric sensors by electrochemical polymerisation of monomers (e.g. pyrrole). Any method can be used in combination with other methods.

The parameters for potentiostatic regime were derived (calculated) from galvanostatic procedures and tested in experiment. For the same growth solution and design of sensors, the potential and currents are dependent on each other.

The potential recorded at the certain applied current can be applied in potentiostatic regime would give approximately the same current as in galvanostatic procedure.

The exact values in each polymerisation method can slightly vary depending on the properties of the conductive or semi-conductive layer, but in general all procedures give comparative results and can be successfully applied to any type of electroconductive or semi-electroconductive support.

Parameters for the polymerisation process can be calculated using either the geometric surface area or the electrochemical surface area of the sensors onto which the polymer is to be deposited.

Various sensor designs have been tested by the inventors. A preferred design of sensor consists of a screen printed circular electrode with a diameter of 1.5 mm² giving a geometric area of 1.77 mm². Other designs may be envisaged and the invention is not to be construed as limited to this particular design. The method used for the calculation of the electrochemical surface area was by placing the electrode in a solution with a redox species (e.g. 5 mM ferrocyanide) and a supporting electrolyte (e.g. 0.1 M NaNO₃). The potential of the electrode is stepped from a potential where no current flows to a potential where all the reduced species is oxidised and the resulting current is recorded with time (chronoamperometry). The shape of the current response with time is given by the Cottrell equation:

$$i=(nFACD^{0.5})/(\pi^{0.5}t^{0.5})$$

Where n=number of electrons transferred=1, F=Faraday (96480 C mol), A=surface area of electrode, D=diffusion coefficient of reduced species, C=concentration of reduced species, i=current, t=time. If the current is plotted against $t^{-0.5}$ then the data should be linear and the area can be calculated from the slope. Alternative methods of estimating the electrochemcial surface area can also be used.

A preferred potentiodynamic method comprises the steps of:
a) preparing an aqueous solution for electrochemical polymerisation comprising monomers (e.g. pyrrole) at a concentration in the range of 0.002-0.05M, and a supporting electrolyte, which also serves as a doping agent, at a concentration in the range of 0.00.01-0.005M
b) assembling an electrochemical polymerisation cell comprising the solution for electrochemical polymerisation, an auxiliary electrode, a reference electrode and one or more electrodes to be coated with a polymer film, wherein the electrodes to be coated comprise a conducting or semi-conducting layer;
c) applying a cyclic voltage in the range −0.2-15+2.0 V (vs Ag/AgCl reference electrode) between the electrode(s) to be coated and the reference electrode to coat the electrode(s) with a polymer film by the electrochemical synthesis of polymer from the electrochemical polymerisation solution.

A preferred potentiostatic method comprises the steps of:
a) preparing an aqueous solution for electrochemical polymerisation comprising monomers (e.g pyrrole) at a concentration in the range of 0.002-0.05M, and a supporting electrolyte, which also serves as a doping agent, at a concentration in the range of 0.0001-0.005M
b) assembling an electrochemical polymerisation cell comprising the solution for electrochemical polymerisation, an auxiliary electrode, a reference electrode and one or more electrodes to be coated with a polymer film, wherein the electrodes to be coated comprise a conducting or semi-conducting layer;
c) applying a constant potential in a single or multiple potential steps at the range 0-3 V between working electrode(s) to be coated and reference electrode for defined period of time such that final quantity of electricity passed through the working electrode(s) will lie in a range 10-250 mC/cm²;

This invention also includes a galvanostatic regime of electrochemical synthesis as an alternative to the potentiodynamic one. In this case the quantity of electricity passed through working electrode(s) to be coated lying within range 10-250 mC/cm² (preferably 10-60 mC/cm²) is a result of applying a constant current with given current density between working electrode(s) and auxiliary electrode for defined period(s) of time. The single or multiple current steps can be used. The current density can be varied within the range 0.01-1 mA/cm².

The present invention provides a galvanostatic method for producing highly sensitive polymer-coated potentiometric sensors by electrochemical polymerisation, which comprises the steps of:
a) preparing an aqueous solution for electrochemical polymerisation comprising monomers (e.g. pyrrole) at a concentration in the range of 0.002-0.05M; and a supporting electrolyte, which also serves as a doping agent, at a concentration in the range of 0.0001-0.005M;
b) assembling an electrochemical polymerisation cell comprising the solution for electrochemical polymerisation, an auxiliary electrode and one or more electrodes to be coated with a polymer film, wherein the electrodes to be coated comprise a conducting or semi-conducting layer;
c) applying a constant current in the single or multiple current steps with given current density in a range 0.01-1 mA/cm² between working electrode(s) to be coated and auxiliary electrode for defined period of time such that final quantity of electricity passed through working electrode(s) will lie in the range 10-250 mC/cm² (preferably 10-90 mC/cm²).

The reference electrode can be used to monitor the galvanostatic process or alternatively a two electrode system may be employed in which a separate reference electrode is not used. In addition, combinations of the different regimes can be used in one polymerisation process. For example, in one embodiment firstly the working electrode(s) can be coated with polymer film in galvanostatic regime, then the additional layer of polymer can be applied using the potentiodynamic or potentiostatic regime. The opposite is also possible. It is also possible to combine two or more galvanostatic regimes. These combinations give more flexibility in controlling redox condition of the polymer film.

The use of multiple currents applied for different times in galvanostatic regime allows tailoring redox properties of the polymer film.

The combination of potentiodynamic cycle(s) or potentiostatic step(s) and galvanostatic step(s) can be used to tailor the redox properties of the polymer film.

The possibility to tailor redox properties by combining more than one polymerisation regime and use of multiple successive currents in galvanostatic regime for preparation of biosensors has not been previously described and is a novel part of this invention.

The method of the invention may be used for applying a polymer film onto a single electrode or a number of electrodes (greater than one) in one step. The ability to coat multiple electrodes in a single polymerisation reaction increases reproducibility and decreases the cost of the manufacturing process. In contrast to previous works, where only a single electrode was coated, the authors of the present invention connect a number of conductive or semi-conductive electrodes to be coated in one block with one single electrical contact, in an electrochemical polymerisation cell, comprising an auxiliary electrode and-for potentiodynamic and potentiostatic regimes-the reference electrode and the solution for electrochemical polymerisation. All electrodes to be coated behave as one single working electrode. Theoretically the number of electrodes to be coated is not limited and can reach tens or even hundreds at a time.

The inventors have further observed that highly sensitive polymer-coated sensors can be produced with the use of combinations of electrochemical polymerisation regimes and/or the use of multiple current or potential steps in the polymerisation regime, without limitation to the use of low (<0.05 M) concentrations of monomer in the electrochemical polymerisation solution.

Therefore, the invention also relates to multi-step methods for electrochemical polymerisation using combinations of electrochemical regimes and/or electrochemical regimes with multiple current or potential steps.

In particular, the invention relates to the following:

A method for producing highly sensitive potentiometric sensors by coating of electrically conductive electrodes with an electroconductive polymer, where two or more current steps are applied in a galvanostatic regime.

A method for producing highly sensitive potentiometric sensors by coating of electrically conductive electrodes with an electroconductive polymer, where two or more potential steps are applied in a potentiostatic regime.

A method for producing highly sensitive potentiometric sensors by coating of electrically conductive electrodes with an electroconductive polymer, where two or more polymerisation regimes, preferably selected from galvanostatic, potentiodynamic, potentiostatic, or other electrochemical regimes, are applied.

Preferred galvanostatic, potentiodynamic, potentiostatic regimes are those described above in connection with the first aspect of the invention.

As aforesaid, in these methods no limitation is placed on the concentration of monomers or background electrolyte used in the electrochemical polymerisation solution. Thus, the methods can be used with the higher concentrations of monomers described in WO 00/11473.

The scope of the invention extends to polymer-coated potentiometric sensors produced according to the methods of the invention, and also to use of these sensors. In particular, the potentiometric sensors may be used in methods for electrochemical detection of analytes (such as those described in WO 00/11473, WO 96/02001, etc.), also in methods for potentiometric detection of enzymatic activity (e.g. methods for measuring the activity of enzymes positioned proximal to the sensor surface) and in methods for potentiometric analysis of whole cells (for example using the techniques described in the applicant's co-pending application GB 0207116.5).

In a further aspect the invention also provides a method of treatment of electroconductive polymer-coated sensors after the deposition of the polymer film to increase both long-term stability and analytical sensitivity of sensors. This treatment may be applied to sensors prepared according to the method of the invention, described above, but may also be applied to polymer-coated potentiometric sensors prepared according to prior art methods of electrochemical polymerisation (see WO 96/02001, WO 0.00/11473, etc).

The treatment method comprises two stages. The first stage is a thorough wash of the polymer-coated sensors by de-ionised water after the electrochemical polymerisation. At this stage non-embedded dopant anion and traces of monomer(s) are eliminated from the polymer film. Removal of a monomer(s) is necessary, because monomers can be oxidised during the storage changing the intrinsic redox properties of the polymer film. Removal of non-embedded dopant ion is also necessary, because the mobile counterion can compromise the metallic properties of the polymer [22, 23] decreasing redox sensitivity. Particularly, an excess of sodium dodecylsulphate denatures protein molecules [16] and decreases adsorption of biomolecules. That could be a negative point for further immobilisation of biomolecules within or onto a polymer film.

The second stabilising step is a removal of unbound water from the polymer film. It is very important, because interactions of unbound water with the polymer change the intrinsic redox properties of the polymer film over a period of time. This is why there are many publications regarding the instability of polymer (e.g. polypyrrole) films over a period of time because the most popular storage method (i.e., in wet-format) [13, 16, 32, 35, 41] leads to instability of the electrochemical characteristics and non-reproducibility of the results of the potentiometric (or other electrochemical) measurements.

These two treatment steps allow sensors to be stored for a long time without changes of their working characteristics, which is very important for the commercial manufacture of sensors.

Another reason why the polymer-based sensors produced according to the method described in the present invention are stable for a long period of storage, is because the polymer films are much thinner than commonly used ("translucent" films). In such thin films the post-polymerisation processes end very quickly and do not further affect the polymer properties.

A further aspect of the invention relates to a method for testing the sensitivity of the polymer-based sensors produced by the method described above. This test can show up very small differences in sensor performance and enhance the ability to tailor the sensors properties. These differences could not be differentiated by generally applied electrochemical procedures, for example measuring the potential by measuring the open circuit potential of the sensors in an electrolyte solution.

It is necessary to have a universal, reproducible and quick test for sensitivity of the obtained sensors in order to evaluate reliably the relationship between conditions of the preparation of the sensors (polymerisation procedure and following treatment) and their analytical sensitivity. This test can also be used as a quality control for all types of sensors and for the future sensor manufacturing process.

The authors of the present invention have found that the reaction between immobilised streptavidin and biotin-labelled horseradish peroxidase (HRP) is a simple, quick and reliable test suitable for testing the analytical sensitivity of the sensors. All components for this test are commercially available and certified.

Therefore, the invention provides a method for testing the analytical sensitivity of a polymer-coated potentiometric sensor, which method comprises the following consecutive steps:

(a) coating the sensor with streptavidin by passive adsorption;
(b) applying a sucrose protective film to the streptavidin coated sensor;
(c) bringing the sensor obtained in step (b) into contact with a solution containing a known concentration of biotin-labelled horseradish peroxidase for a defined period of time;
(d) monitoring the electric potential difference between the sensor and a reference electrode when both are immersed in a basic electrolyte solution;

(e) replacing the basic electrolyte solution with an enhancer electrolyte solution having identical composition to the basic electrolyte solution except that it additionally contains a substrate for horseradish peroxidase and monitoring the electric potential difference between the sensor and reference electrodes when immersed in the enhancer electrolyte solution;
(f) calculating the difference between the electric potential difference measurements obtained in steps (d) and (e) and comparing the result obtained with reference results obtained with use of a pre-defined standard sensor or other sensors evaluated at the same time.

Steps a) and b) can be combined in one step: a drop of Streptavidin in sucrose solution can be placed onto the sensor and dried. Any additional components, e.g. blocking components or stabilisers, can be added to the solution. The washing step may be required before performing the assay.

In a preferred embodiment the basic electrolyte solution used in step (d) may comprise an H-donor.

The above method provides a rapid, standardised potentiometric assay which may be used to quickly evaluate the analytical sensitivity of a given potentiometric sensor and to determine the effect of, for example, changes in the composition of the electrochemical polymerisation solution on the final analytical sensitivity of the sensor. Analytical sensitivity is preferably evaluated relative to a standard or reference sensor, which is selected by the user. The standard or reference sensor is chosen merely to provide a basis line (or reference line) against which other sensors may be compared. The precise characteristics of the reference sensor are not material to the invention.

It is important that assay parameters, i.e. concentrations of reagents, incubation times etc are standardised in order to allow meaningful comparison between results obtained with different sensors. However, the precise values of these parameters are not material and may be selected by the user. The skilled reader will appreciate that suitable assay parameters may be determined by routine experiment. One example of a model assay is given in the accompanying examples.

The standardised assay is a development of the method described in the applicants' International application WO 00/11473 and steps (a) and (c) to (e) may be performed as described in WO 00/11473, the contents of which are incorporated herein by reference.

Step (b) results in coating of the sensor with a protective layer of sucrose. This step is important as the sucrose layer prevents loss of activity of the adsorbed streptavidin and also helps to prevent oxygen and moisture access to the polymer layer. As illustrated below, the sucrose coating is conveniently applied by dipping the sensor into a sucrose solution (typically 1-25%, most preferably 10% sucrose) or applying a drop of sucrose solution containing streptavidin, if the steps (a) and (b) are combined, then drying the sensor (preferably at 30-40° C. for approximately 8-12 hours).

The utility of applying a coating of sucrose to the sensor is not limited to the standard model assay system. Rather, any potentiometric sensor comprising a conductive electrode coated with a layer of conductive polymer, particularly polypyrrole, can be coated with a protective layer of sucrose. Furthermore, other protective substances can be used instead of sucrose with equivalent effect.

Therefore, in a further aspect the invention provides a potentiometric sensor comprising an electroconductive electrode coated with an electroconductive polymer, characterised in that a coating of a protective substance is applied on top of the electroconductive polymer.

Suitable protective substances are those that act as protein stabilisers. Suitable examples include, inter alia, trehalose, inositol, cellobiose and lactitol, as well as sucrose. It is also possible to use mixtures of these substances with polymers such as dextrans or polyglycols. The protective coating is generally applied by immersing the sensor in a solution of the protective substance or by any other suitable method, e.g. placing a drop of protective solution or screen-printing (e.g. a 1-25% solution of trehalose, inositol, cellobiose, lactitol or sucrose) and then drying the sensor. Any other substances to be applied to the sensors, such as bioreceptors, e.g. streptavidin, antibodies, peptides, etc., as well as blocking agents, stabilisers, etc. can be added to the protective solution and applied at this step.

In a further aspect the present invention provides a potentiometric sensor comprising an electroconductive polymer, characterised in that it can be used in any analysis with potentiometric detection step, e.g. enzymatic assays or cell analysis, where the measurable change in potential of the polymer layer due to redox, pH, or ionic changes due to enzymatic activity or cell metabolic activity occurs. For example, cells can be attached to the surface by growing there directly or via affinity interactions and the change in potential can be detected by potentiometric measurement described in the present invention.

DETAILED DESCRIPTION OF THE INVENTION

Figure 1A:
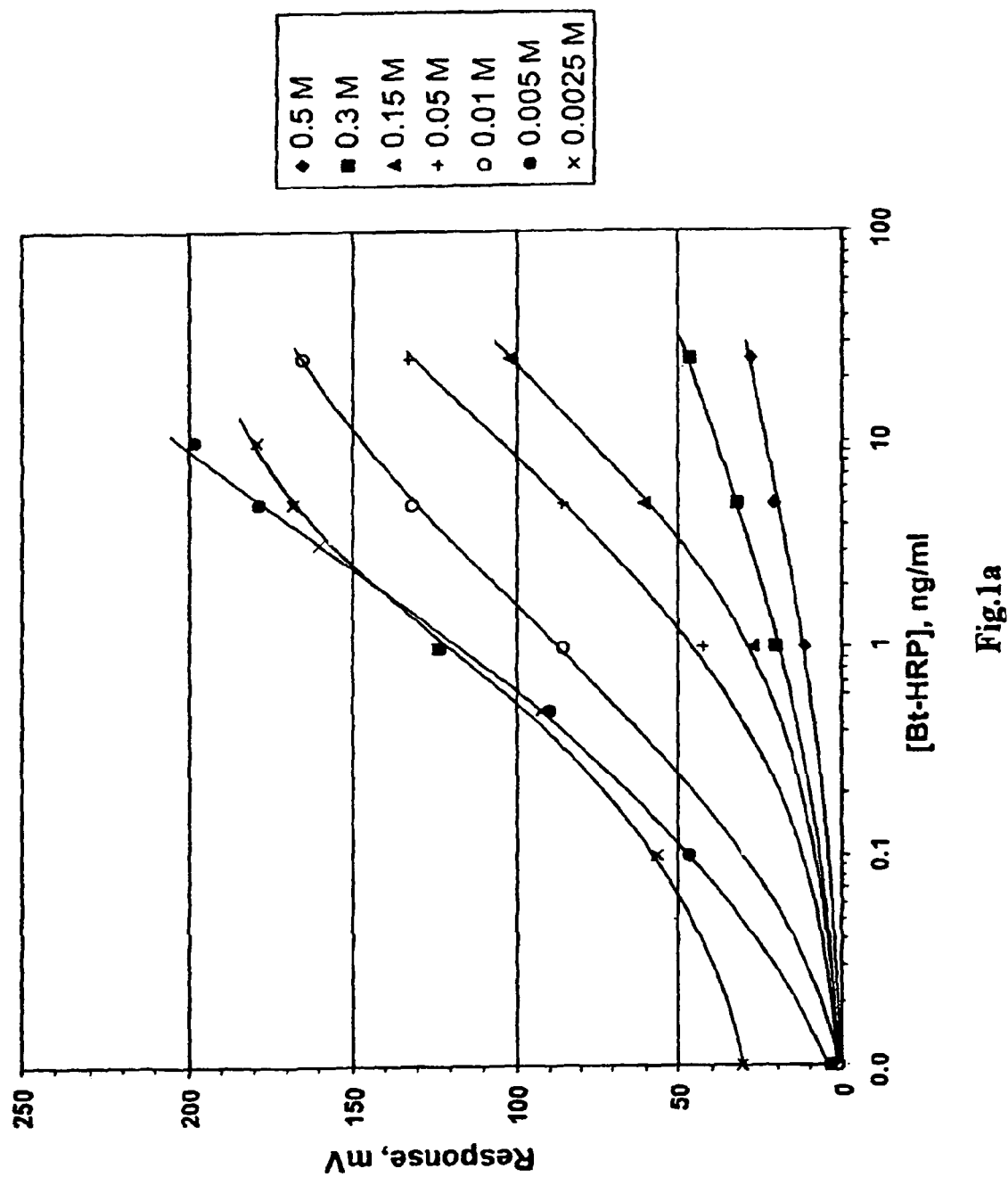
FIG. 1 illustrates the relationship between the potentiometric response from a polypyrrole potentiometric sensor coated with streptavidin and the concentration of biotinylated horseradish peroxidase (Bt-HRP) for potentiometric sensors coated with polypyrrole films, grown from polymerisation solutions containing different concentrations of pyrrole.

The method of the invention is used for the production of highly sensitive potentiometric sensors by coating of electrically conductive electrodes with an electroconductive polymer.

The electrically conductive electrode to be coated with electroconductive polymer may be essentially any suitable electrode comprising a conductive or semi-conductive layer.

Suitable electrodes include standard potentiometric electrodes possessing metallic or quasi-metallic conductivity which are stable in aqueous media. The electrode preferably consists of a plastic support with an adhesive layer (carbon or copper) with a conductive substrate (preferably gold) electrochemically plated or directly screen-printed onto the plastic support. The reference electrode, e.g. Ag/AgCl reference electrode, which is required for potentiometric detection step can be placed on the same support as the sensing electrode by any method, for example screen-printed. An external commercial reference electrode can be used as well.

Any lay outs of a final sensor product are possible, for example, "dip-stick", multiwell plates containing integrated electrochemical sensors for use in methods of electrochemical analysis.

The aqueous electropolymerization solution typically comprises monomeric units of the electroconductive polymer at a concentration in the range of from 0.002 M-0.05 M, preferably 0.002 M-0.02M, more preferably 0.0025 M-0.15 M, more preferably 0.005 M-0.01 M in distilled water (e.g. MilliQ) and a supporting electrolyte at a concentration in the range from 0.0001 M-0.005 M, preferably, 0.0001 M-0.002, preferably 0.0001 M-0.0015 M, more preferably 0.0001-0.001 M. Other polar solvents may be substituted for distilled water.

Suitable monomers include pyrrole, furan, thiophene or other, with pyrrole being most preferred. Combinations of two or more of these monomers may also be used, leading to the production of conductive copolymers.

The preferred supporting electrolyte is sodium dodecylsulphate but other electrolytes, the anions of which are immobile within the polymer films, may be used. The electrolyte also serves as a doping agent.

Most preferably the electrochemical polymerisation solution consists of an aqueous solution of monomers and supporting electrolyte. However, it is to be understood that other components may be added to the polymerisation solution such as, for example, components which provide specific functional groups which can be used as linkers for bioreceptors or for chemical modification of the sensor surface (see WO 00/11473).

The ratio between the concentrations of monomers and supporting electrolyte in the polymerisation solution is preferably in the range from 2:1 to 30:1, and more preferably in the range from 5:1 to 30:1. A ratio of approximately 25:1 is the most preferred.

The most preferred compositions, though not limiting to the overall scope of the invention, are 0.005-0.01 M monomers (pyrrole being most preferred) with 0.0002 M electrolyte (SDS being most preferred) or 0.0075-0.01 M monomers (pyrrole most preferred) with 0.0017 M electrolyte (SDS most preferred).

The electrochemical polymerisation is carried out in a two- or three-electrode system comprising of electrode(s) to be coated (also referred to herein as the "working electrode"), the auxiliary electrode and the reference electrode. In the case of the two electrode system (galvanostatic regime) the reference electrode would not be used. Suitable assemblies have been described in the prior art (see WO 00/11473 and references contained therein). Multiple working electrodes can be combined in a block with one electrical contact.

The auxiliary electrode is preferably made of platinum, other noble metal or other inert conductive material such as graphite or carbon. The auxiliary electrode should have a surface area greater than total area of all working electrodes [53]. In order to decrease the uncompensated solution resistance in the polymerisation solution, the reference electrode should be positioned as close as possible to the working electrodes. [20, 21, 53]. A constant distance between the working electrodes and the reference electrode is preferable. The conventional Ag/AgCl or calomel electrode can serve as a reference electrode.

A potentiostat may be used for performing the electrochemical synthesis. In case of potentiodynamic regime a cyclic voltage within the range of −0.2-+2.0 V (vs Ag/AgCl reference electrode) at a scan rate of preferably 50-100 mV/s for preferably 1-15 cycles is applied between the reference electrode and the working electrode(s) to be coated. The current is recorded at the auxiliary electrode.

The shape of the voltammetric curve and total quantity of electricity passed through the working electrode(s) are controlled parameters for polymer formation. The quantity of the electricity passed during each cycle must not differ more than 5% from the first cycle.

In case of the galvanostatic regime one or more constant current steps can be applied between the working electrode(s) to be coated and the auxiliary electrode within the range of 0.01-1 mA/cm$^2$ for time of 100-1000 s. The number of applied current steps is not limited. One to five steps have been used by authors so far. The preferred total duration of polymerisation is 150-600 s.

The galvanostatic regime is more preferable. It is less expensive and easier to control than other regimes, and the equipment is less sophisticated. The use of different applied currents allows tailoring of the redox properties of the polymer films with a very high precision. The use of the galvanostatic regime also allows precise control of an oxidation level of the resulting polymer film.

In some particular cases the sequential use of galvanostatic and potentiodynamic or potentiostatic (and vice versa) regimes in one polymerisation process is possible. For example the main polymer film is formed at the low potential using small constant current in galvanostatic regime and after that the additional amount of polymer is grown in potentiodynamic regime using high upper potential. The conductive polymer can be further conditioned by the use of low potential eg 0V (vs Ag/AgCl) or by using a current step of 0 A for a period of 1-300 s.

After the electrochemical synthesis the polymer-coated sensors are preferably washed with deionized water until monomer and sodium dodecylsulphate are not traceable.

After the washing step the unbound water must be removed from the polymer film. This may be done in several ways. The simplest way is to heat the sensors in an incubator for at least 8 hours. The temperature can be varied depending on the thickness of polymer film within the range 25-50° C., preferably 30-40° C. This range is very important because on the one hand the unbound water cannot be completely removed at temperature lower than 25° C., on the other hand a high temperature (more than 50° C.) can damage the polymer film. Another possibility for removing water is lyophilization.

The washing and drying steps described above may also be used to treat polymer-coated electrodes prepared by the prior art methods of electrochemical polymerisation (see WO 96/02001, WO 00/11473 and references described therein). This treatment provides particular advantages in relation to long-term storage of the electrodes, as described above.

The main application for the polymer-coated electrodes obtained by the methods described above is production of highly sensitive potentiometric biosensors e.g. chemical-, enzyme- or immunosensors. Any biological receptor(s) can be immobilised onto a sensor using well known techniques for solid phase coating. Any form of redox, pH-changing or acidification assay can be performed using these sensors including cell analysis.

In order to evaluate and control the redox sensitivity of the sensors the authors of the present invention propose to use a model assay based on the use of polymer-based sensors coated with streptavidin, which react with biotinylated horseradish peroxidase. It has been mentioned above that the use of commonly applied electrochemical procedures is not suitable for testing the properties of the sensors as it is not possible to distinguish the differences in properties at the required level. An immunoassay helps to evaluate the redox properties and accordingly analytical sensitivity of the sensors prepared using different polymerisation regimes.

The techniques of coating the polypyrrole layer with streptavidin are described in detail in the inventors' International application WO 00/11473. The streptavidin concentration in the coating solution may be varied from 2-100 µg/ml depending on the method of coating. In addition, in the present invention a protective sucrose layer is applied on the sensors coated with streptavidin followed by drying of the sensors.

The coating with streptavidin and application of protective layer can be combined together. In the latter case a drop (0.1-10 µl) of the protective solution containing streptavidin is placed onto the sensor and dried. Other methods, e.g. screen-printing may be used.

The procedures for incubation with an analyte are described in WO 00/11473. A wide range of aqueous buffers with different pH can be employed for HRP solution preparation. The concentration of biotinylated HRP is varied within range 0-100 ng/ml. The typical set of concentrations is: 0, 0.02, 0.05, 0.1, 0.2, 0.5, 1.0, 2.0, 5.0, 10.0, 50.0, 100.0 ng/ml. The incubation time may be 2-60 min.

The potentiometric measuring procedure, as well as a calculation of an analytical result, is described in detail in WO 00/11473.

It is well known that HRP requires the use of an H-donor to speed up the enzymatic reaction. However, in WO 00/11473 only H-donors which are commonly used in routine immunoassays with optical detection were mentioned. All these H-donors change their colour as a result of the enzyme reaction. This colour-change is not required for the potentiometric measurement. In the latter case only the magnitude of change in redox state of the sensing element, e.g. polymer film as a result of interaction with HRP is important. The authors of the present invention have found that a number of colourless substances can serve as H-donors for HRP and provide sufficient change in redox state to perform potentiometric measurement. Suitable H donors are those which give a high magnitude change in redox state as a result of the interaction with horseradish peroxidase. Most preferably the H-donor will be an H-donor providing a sensor potentiometric response of at least 10 mV as a consequence of interaction with horseradish peroxidase under the defined conditions of the model assay. Examples of suitable colourless H-donors are coniferol, guaiacol, MBTH. The concentration of H-donors used in potentiometric measurement, depending on the particular H-donor, may be varied within the range 0.1-100 mM. It is possible to extend or shift the measuring range for particular analyte by changing just the H-donor and/or its concentration in the substrate system.

In WO 00/11473 hydrogen peroxide served as the HRP substrate. Being a strong oxidising agent hydrogen peroxide may affect measuring results by interfering with the polymer layer or underlying electrode. In the present invention it may be replaced with a substrate which is an organic or non-organic peroxide. Suitable substrates include methylhydroperoxide, ethylhydroperoxide or p-nitroperoxybenzoic acid and sodium perborate. The concentration of the substrate varies depending on the nature of substrate within range of 0.0005-0.1%. In the case of sodium perborate the preferred concentration is 0.03%.

Obviously the utility of these H-donors and peroxide substrates is not limited to the model assay system for evaluation of redox sensitivity and quality control described herein. Indeed these H-donors and substrates may also be used for potentiometric analysis of various analytes, for example using methods analogous to the sandwich and competitive potentiometric analysis methods described in WO 00/11473.

These potentiometric analysis methods are analogous to the model assay system except that the surface of the sensor is modified with a biomolecule having specific binding affinity for the analyte of interest rather than streptavidin (NB the analyte-specific binding molecule may be attached to the sensor via a biotin/streptavidin interaction with streptavidin adsorbed to the sensor or immobilised in the polymer coating, as described in WO 00/11473). The features of potentiometric assays based on the use of an enzyme label (e.g. peroxidase) will be understood with reference to WO 00/11473. Enzymatic labels other than the HRP enzyme can be used (e.g. other peroxidases, glucose oxidase or catalase) as any enzymatic process involves the electron transfer, which in its turn change the potential of the sensor.

Typical "sandwich" potentiometric methods of electrochemical detection using an enzyme label (such as the methods described in WO 00/11473) comprise the steps of:

(a) providing a potentiometric sensor having an electroconductive polymer coating, the coating having immobilized therein or adsorbed thereto receptors which are capable of binding to the desired analyte to be detected in the sample;

(b) contacting the sensor with a test solution comprising the sample so that the said analyte binds to said immobilized or adsorbed receptors;

(c) contacting the sensor with a solution comprising secondary receptors capable of binding to said analyte at a site spatially distinct from the site of binding to immobilized or adsorbed receptors, said secondary receptors being conjugated with at least one enzyme;

(d) monitoring the electric potential difference between the sensor and a reference electrode when both are immersed in a basic electrolyte solution;

(e) transferring the sensor and reference electrode to an enhancer electrolyte solution having identical composition to the basic electrolyte solution except that it additionally contains substrate for the enzyme(s) and monitoring the electric potential difference between the sensor and reference electrodes when immersed in the enhancer electrolyte solution;

(f) calculating the difference between the electric potential difference measurements obtained in steps (d) and (e) and relating the result obtained to the concentration of analyte in the sample.

Whereas, typical "competitive" potentiometric methods of electrochemical detection using an enzyme label (such as the methods described in WO 00/11473) comprise the steps of:

(a) providing a potentiometric sensor having an electroconductive polymer coating, the coating having immobilized therein or adsorbed thereto receptors which are capable of binding to the desired analyte to be detected in the sample;

(b) contacting the sensor with a test solution comprising the sample so that the said desired analyte binds to said immobilized or adsorbed receptors;

(c) contacting the sensor with a solution comprising competing molecules capable of binding to said immobilized or adsorbed receptors, said competing molecules being conjugated with at least one enzyme;

(d) monitoring the electric potential difference between the sensor and a reference electrode when both are immersed in a basic electrolyte solution;

(e) transferring the sensor and reference electrode to an enhancer electrolyte solution having identical composition to the basic electrolyte solution except that it additionally contains substrate for the enzyme(s) and monitoring the electric potential difference between the sensor and reference electrodes when immersed in the enhancer electrolyte solution;

(f) calculating the difference between the electric potential difference measurements obtained in steps (d) and (e) and relating the result obtained to the concentration of analyte in the sample.

The invention provides methods having all the features of the typical assays listed above, characterised in that (i) a peroxidase enzyme label is used, optionally in conjunction with further enzyme labels selected from peroxidases (e.g. horseradish peroxidase), glucose oxidase and catalase, and (ii) the basic and enhancer electrolyte solutions comprises an H-donor exhibiting a high magnitude of change in its redox state as a result on interaction with the peroxidase, thereby providing a high potentiometric sensor response.

Preferably the H-donor will provide a sensor potentiometric response of at least 10 mV for an analyte concentration interest as a consequence of interaction with the peroxidase.

Most preferred H-donors include, but are not limited to, coniferol, guaiacol and MBTH.

Assays may also be performed using glucose oxidase or catalase as the enzyme label without peroxidase, but in this case it is not necessary to add an H-donor to the electrolyte.

The invention further provides methods having all the features of the typical assays listed above, characterised in that (i) the enzyme is a peroxidase (e.g. horseradish peroxidase, and (ii) the enzyme substrate is sodium perborate, hydrogen peroxide or an organic peroxide. In these methods the basic and enhancer electrolyte solutions comprise an H-donor, but the precise nature of the H-donor is not limited.

The possibility to use alternative H-donors (with a peroxidase enzyme label) and different combinations of enzymes (e.g. combinations of peroxidases, catalase, glucose oxidase, etc.) adds additional flexibility for the whole system, expanding the range of possible applications for the present invention.

The invention will be further understood with reference to the following, non-limiting, experimental examples:

EXAMPLES

All reagents were purchased from Sigma if not otherwise stated. Pyrrole purchased from Merck was purified by distillation and stored in aliquots at −20° C.

Example 1

This first example demonstrates the relationship between the concentration of pyrrole, in the solution for the electrochemical polymerisation, and analytical sensitivity of the polypyrrole-based potentiometric sensors.

The working electrodes were custom-made planar electrodes comprising PET (polyethyleneterephthalate) support (~125 µm) with the electro-deposited copper (~17 µm) coated with electrochemically-plated gold (~30 µm). The working area was approximately 1.0 sq mm. Aqueous solutions for electrochemical polymerisation comprised 0.0002M SDS (sodium dodecylsulphate) serving as a supporting electrolyte and the following pyrrole concentrations: 0.55M, 0.3M, 0.15M, 0.05M, 0.01M, 0.005M, 0.0025M. One of solutions was placed in the cell for electrochemical polymerisation comprising the auxiliary platinum electrode and the reference electrode (BAS). Eight electrodes combined in one block having one electrical contact were placed in the cell, the working area immersed in the solution. In order to provide uniform current density all electrodes were placed in parallel to the auxiliary electrode. In order to minimise ohmic drop the reference electrode was located at the nearest possible distance from the working electrodes. The electrochemical polymerisation was carried out using µAutolab II potentiostat-galvanostat (EcoChemie), by applying cycling voltage within −0.2-+1.7 V four times with the scan rate 0.05 V/sec.

After polymerisation, the sensors were placed in a reservoir containing deionized water, and the water was replaced systematically with fresh (every 15 min for 3 hours). After washing, the sensors were placed in an incubator at 37° C. for 24 hours.

Redox sensitivity was tested using a model assay (polypyrrole-based sensors coated with streptavidin react with biotinylated horseradish peroxidase).

Dried sensors were placed in streptavidin solution (40 µg/ml streptavidin in potassium phosphate buffer (0.05M, pH 8.0) at +4° C. for 24 hours. After adsorption the sensors were placed in 10% aqueous sucrose solution for 1-2 min and then dried. After this step the sensors can be foiled and kept for extended period of time. The estimated period is at least 12 months.

In this example the protective sucrose film was removed by washing with the reaction buffer (0.1M potassium phosphate buffer, pH 7.8) before the next stage of the analysis. However, it is not essential for the sucrose layer to be removed at this stage. The sucrose-coated sensor can be brought into contact with solution containing the analyte (in this case biotinylated HRP). Sucrose is highly soluble and will dissolve very quickly. Moreover the presence of sucrose in the reaction vessel does not affect the assay itself. In the present example, after washing out the protective sucrose film the streptavidin-coated sensors were incubated with various concentrations of biotinylated HRP in the reaction buffer, washed and left in it until the potentiometric measurement.

The method of potentiometric measurement, described in detail in WO 00/11473, combines two steps. Typically, the first potentiometric measurement is taken (vs Ag/AgCl reference electrode) in the first electrolyte solution (additionally called the Basic Solution) containing an H-donor. The second potentiometric measurement is taken (vs Ag/AgCl reference electrode) in the second electrolyte solution (additionally called the Enhancer Solution), which has the same chemical composition as the Basic Solution, but with the addition of the enzyme substrate. The difference between two potentials related to the concentration of an analyte in a sample is measured in millivolts. The presence of H-donor in the Basic Solution is desirable in order to eliminate the contribution of H-donor itself to the final result.

The measurements were taken using a measuring device comprising the measuring cell (constructed in these laboratories). The sensor was placed in the measuring cell, the Basic Solution was pumped in, and then replaced with the Enhancer solution according to set parameters. The result was calculated by custom-designed software.

In this example the Basic Solution was 100 mM OPD (o-phenilenediamine) in 0.05M sodium citrate buffer, pH 5.0. Sodium perborate (0.03%) was used as a substrate for HRP in the Enhancer Solution. The first potentiometric measurement was taken at 20 sec; the second potentiometric measurement was taken at 60 sec.

The relationship between the potentiometric response and the concentration of HRP for the sensors with the polypyrrole films, grown from the solutions with different concentrations of pyrrole, is shown in FIG. 1a.

Figure 1B:
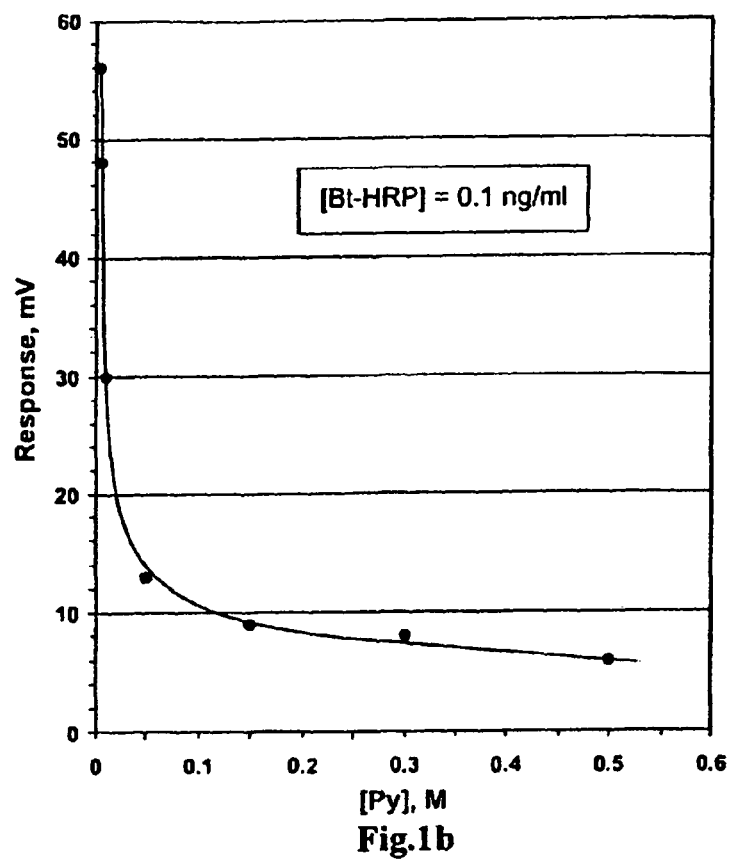
Figure 1C:
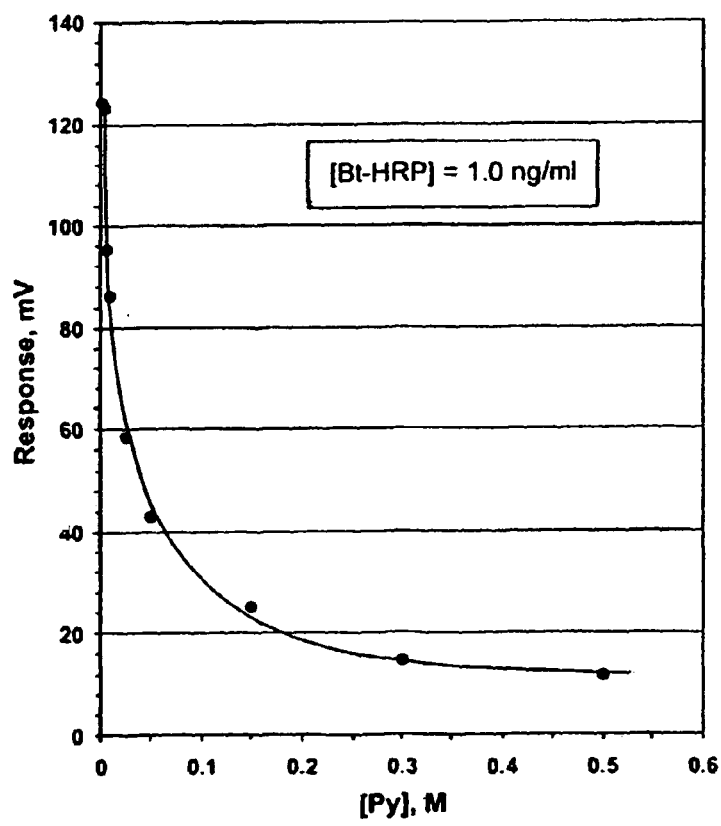
Figure 1D:
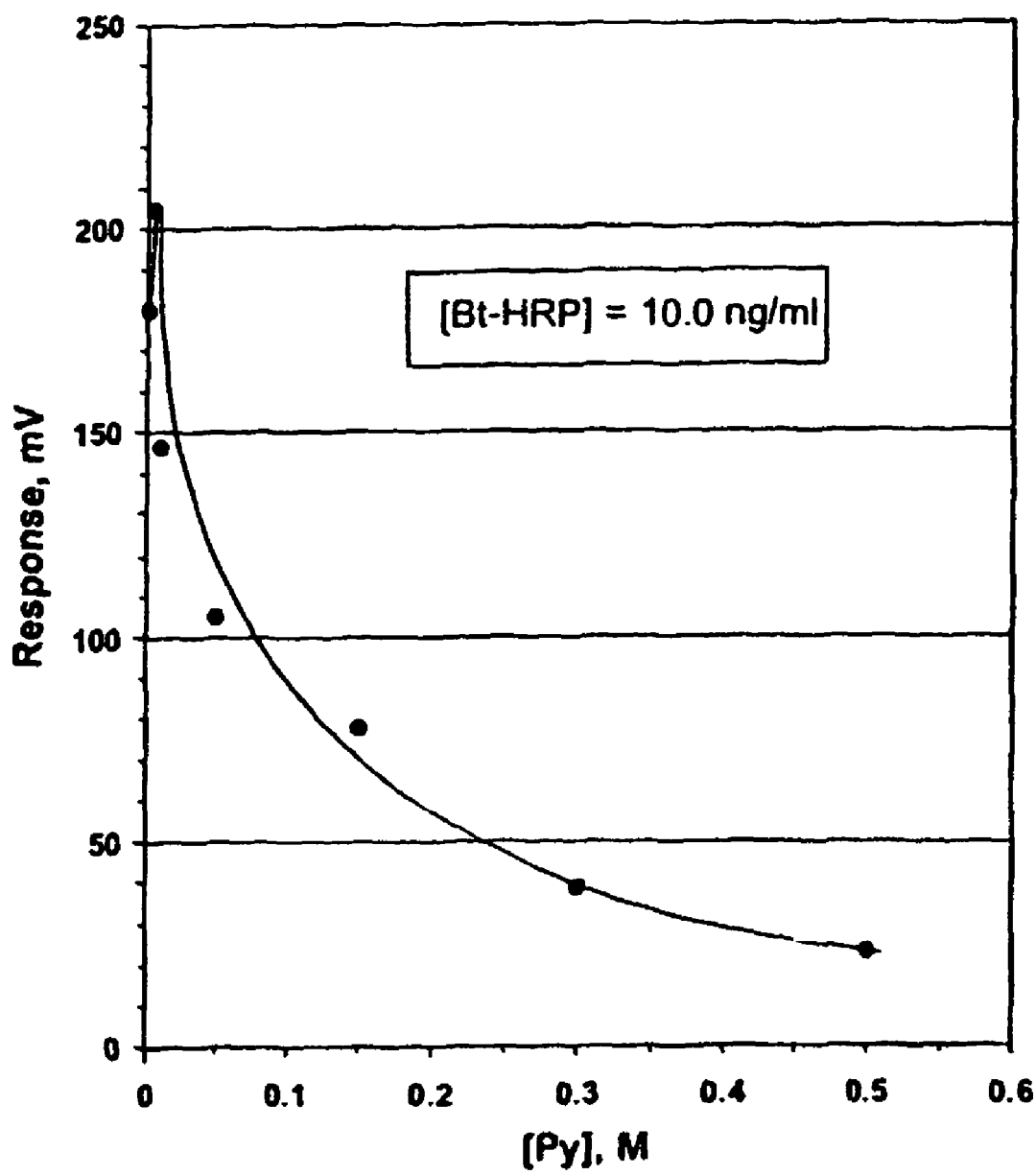

The response of polypyrrole-based sensor is strongly dependent on the concentration of the monomer in the solution for electrochemical polymerisation. The relationship between the signal and the concentration of pyrrole in the polymerisation solution for particular HRP concentration is shown on FIG. 1b (0.1 ng/ml HRP), FIG. 1c (1.0 ng/ml HRP) and FIG. 1d (10 ng/ml HRP).

The signal typically increases with a decrease of the concentration of pyrrole in polymerisation solution. The ultimate increase in signal is observed for the sensors produced from the solutions with 0.0025M-0.015M of pyrrole (0.005M for 10 ng/ml, FIG. 1d).

As mentioned above this effect is observed within the range of pyrrole concentrations, which has not been considered by other researchers for production of highly sensitive polymer-based sensors.

This example demonstrated that the concentration of a monomer in the solution for electrochemical polymerisation is one of the critical factors for production of highly sensitive potentiometric sensors.

Example 2

This example demonstrates the relationship between the concentration of supporting electrolyte in the solution for the electrochemical polymerisation and analytical sensitivity of the polypyrrole-based potentiometric sensors.

The potentiometric sensors were prepared as in Example 1, with the difference, that the monomer concentration in the aqueous solutions for electrochemical polymerisation was fixed (0.005M). SDS (supporting electrolyte) was used in following concentrations: 0.0001M, 0.00015M, 0.0002M, 0.0004M, 0.001M, 0.002M. The sensors were treated after the polymerisation and the analytical sensitivity was tested accordingly as in Example 1 using biotinylated HRP concentrations within the range 0-10 ng/ml.

Figure 2A:
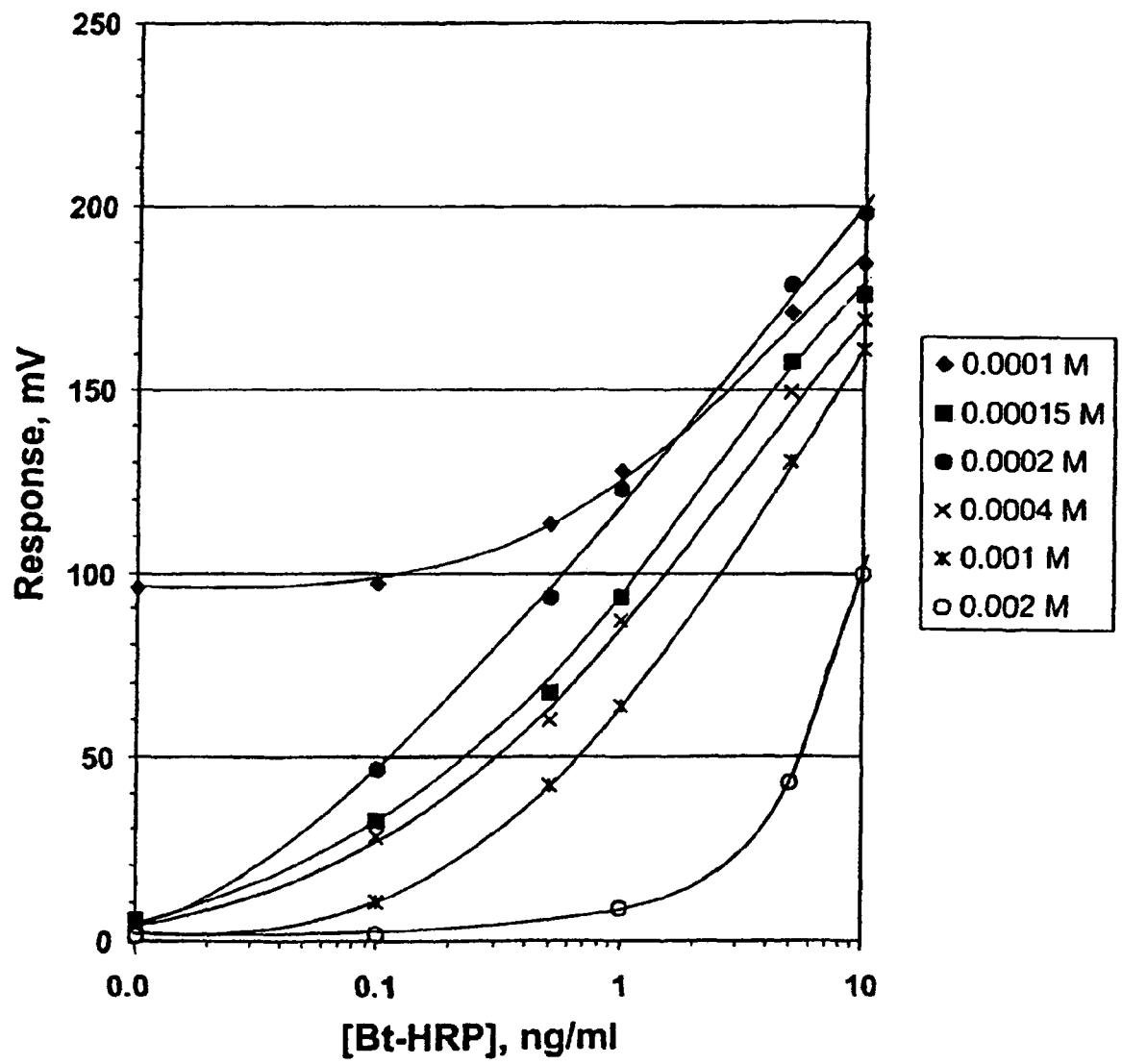
FIG. 2 illustrates the relationship between the potentiometric response from a polypyrrole potentiometric sensor coated with streptavidin and the concentration of horseradish peroxidase (HRP) for potentiometric sensors coated with polypyrrole films, grown from polymerisation solutions containing different concentrations of SDS.

The relationship between the potentiometric response and the concentration of biotinylated HRP for the sensors with the polypyrrole films grown from the solutions with different concentrations of SDS is shown on FIG. 2a. The response of polypyrrole-based sensor is strongly dependent on the concentration of the supporting electrolyte in the solution for electrochemical polymerisation.

Figure 2B:
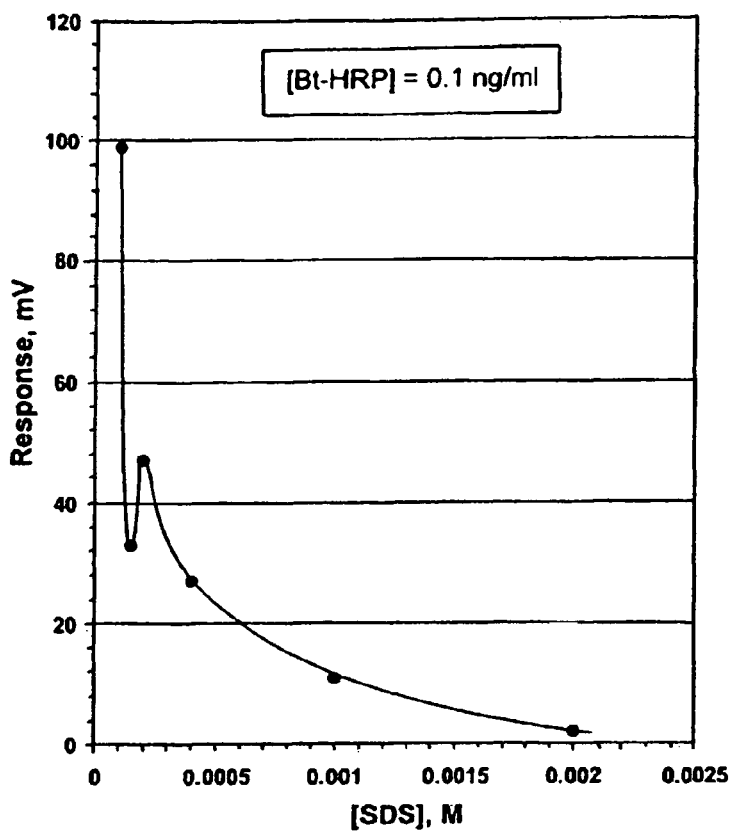
Figure 2C:
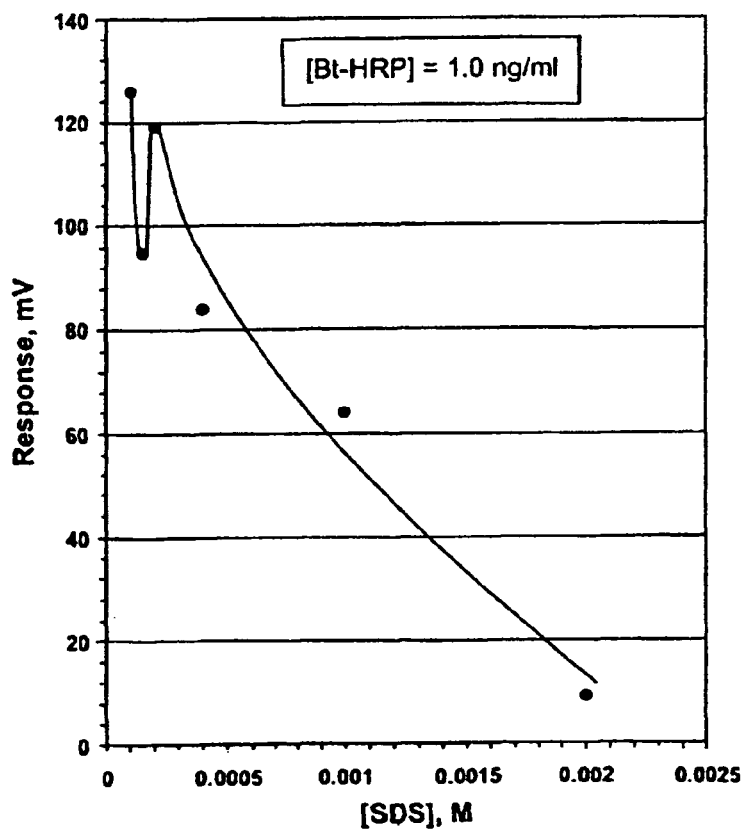
Figure 2D:
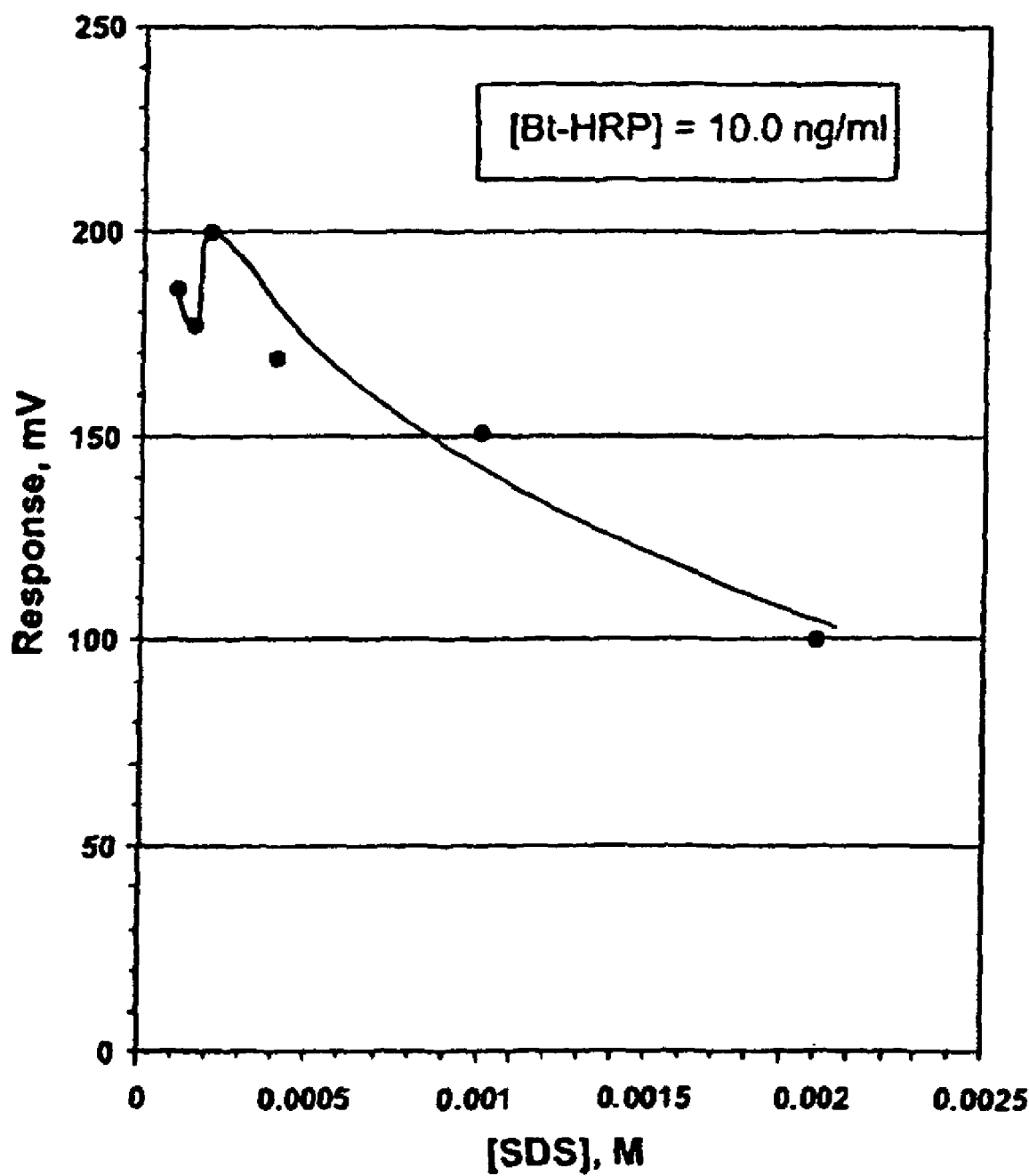

The relationship between the signal and the concentration of SDS in the polymerisation solution for particular biotinylated HRP concentration is shown on FIG. 2b (0.1 ng/ml HRP), FIG. 2c (1.0 ng/ml biotinylated HRP) and FIG. 2d (10 ng/ml biotinylated HRP). The curves have the peaks at 0.0002M SDS, there is a drop at 0.00015M followed by sharp increase in sensor response at 0.0001M for biotinylated HRP concentrations $\leq 1.0$ ng/ml.

The relationship between the SDS concentration in the polymerisation solution and analytical sensitivity of the potentiometric sensors is complex. On the one hand SDS serves as a dopant ion providing certain electrochemical properties to the polymer films, and the changes in SDS concentration result in changes in analytical sensitivity of the sensors (see FIG. 2, a,b,c,d). On the other hand SDS serves as a supporting electrolyte providing certain conductivity to the polymerisation solution and the certain current density, which defines the thickness of polymer films. The polymer films grown from the polymerisation solutions with higher SDS concentration are thicker.

The polymer films formed from the solutions with the lowest SDS concentration (0.0001 M) are patchy. The potentiometric response is partly derived from the polymer as a consequence of the enzyme reaction and partly by exposed gold appeared on the surface as a consequence of substrate presence. The contribution of response of exposed gold is clearly seen at 0 ng/ml biotinylated HRP.

Both examples prove that the concentrations of the monomer and supporting electrolyte and their ratio are critical factors responsible for analytical sensitivity of polymer-based potentiometric sensors. The examples also demonstrate the possibility to tailor the analytical sensitivity and the measuring range by changing the parameters of electrochemical synthesis.

Example 3

This example demonstrates the relationship between parameters of the polymerisation process and analytical sensitivity of polymer-based potentiometric sensors.

40 electrodes were combined in one block having one electrical contact. The electrodes were positioned on the perimeter of a round cell. An Ag/AgCl reference electrode was positioned in the centre of the cell. The auxiliary electrode was platinum gauze fixed to the bottom of the cell equidistant from each of the 40 working electrodes. The circle disposition was chosen in order to provide a uniform current density for all working electrodes. The polymerisation solution with the concentrations of pyrrole (0.005M) and SDS (0.0002M) found optimal in previous experiments (see examples 1 and 2) was used.

The electrochemical polymerisation was carried out using µAutolab II potentiostat-galvanostat (EcoChemie), by applying cycling voltage four times with the scan rate 0.05 V/sec. The bottom boundary potential was −0.2 V (the same as in Example 1). The upper boundary potential was changed within 1.4-2.0 V. The sensors were treated after the polymerisation as described in previous examples and the analytical sensitivity was tested accordingly as in Example 1 using biotinylated HRP concentrations within the range 0-10 ng/ml.

Figure 3:
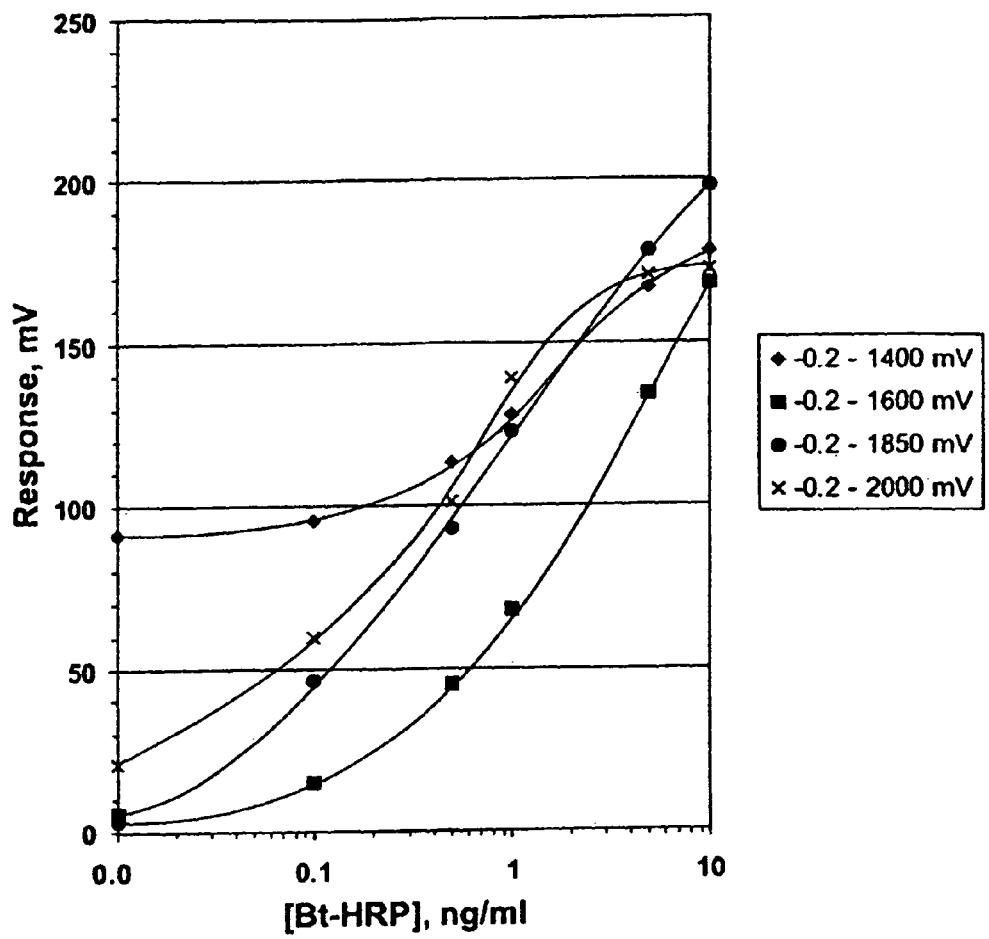
FIG. 3 illustrates the effect of variation in upper boundary potential on the analytical response and the shape of the curve (signal vs HRP concentration) for a polypyrrole-coated potentiometric sensor.

According to the results the analytical response of the sensor and the shape of the curve (signal—HRP concentration) are influenced by upper boundary potential (FIG. 3).

The upper boundary potential is another critical factor for potentiometric sensitivity of the potentiometric sensor. It is responsible for redox state of the polymer film and its thickness, which depends on the quantity of electricity passed per surface area unit.

The example proves one of the main statements of the present invention that the concentrations of the monomer(s) and the supporting electrolyte(s), the ratio between them, the range of applied cyclic voltage synergistically influence analytical sensitivity of polypyrrole-based sensors.

It should be mentioned that the sensors produced by the method described above have higher sensitivity than known potentiometric sensors and can be used for potentiometric analysis of a wide range of analytes.

Example 4

This example demonstrates the influence of the quantity of electricity passed through working electrodes in galvanostatic regime of electrochemical synthesis on their analytical sensitivity.

40 electrodes were combined in one block having one electrical contact. The electrodes were positioned on the perimeter of a round cell. An Ag/AgCl reference electrode was positioned in the centre of the cell. The auxiliary electrode was platinum wire fixed to the bottom of the cell equidistant from each of the 40 working electrodes. The polymerisation solution with the concentrations of pyrrole (0.005M) and SDS (0.0002M) found optimal in previous experiments (see examples 1 and 2) was used.

The electrochemical polymerisation was carried out using μAutolab II potentiostat-galvanostat (EcoChemie), by applying three successive different current densities between electrodes, to be coated, and auxiliary electrode. The current density used was 0.1 mA/cm$^2$, 0.15 mA/cm$^2$ and 0 mA/cm$^2$ for the first, second and third levels respectively. The duration of the first current density was varied within 300-900 s. The duration of the second and last density levels were kept constant (23 and 5 s respectively). Accordingly, the resulting quantity of electricity was 33.5-93.5 mC/cm$^2$.

The resulting sensors were treated after the polymerisation as described in previous examples and their analytical sensitivity was tested accordingly as in Example 1 using biotinylated HRP concentrations within the range 0-10 ng/ml.

Figure 4:
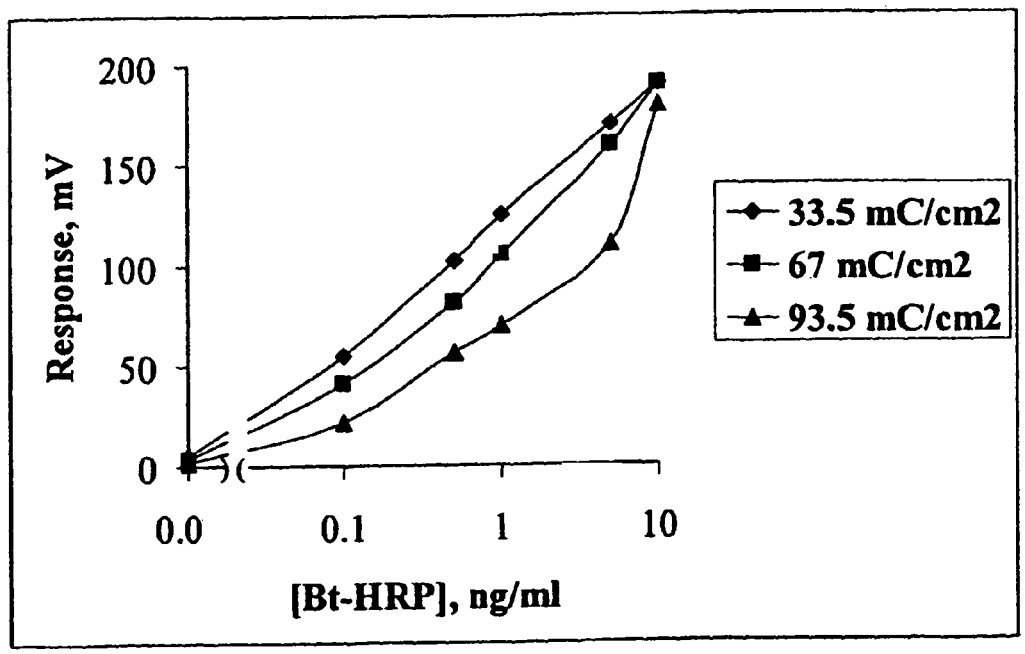
FIG. 4 illustrates the effect of variation in quantity of electricity passed through the working electrode on the analytical response and the shape of the calibration curve for a polypyrrole-coated potentiometric sensor.

The response of the sensor and the shape of the curve "signal—HRP concentration" are dependent on the quantity of electricity passed through electrodes during polymerisation process (FIG. 4).

This example proves one of the main statements of the present invention that the concentrations of the monomer(s) and the supporting electrolyte(s), the ratio between them, the quantity of electricity passed through electrodes during polymerisation synergistically influence analytical sensitivity of polypyrrole-based sensors.

Example 5

This example demonstrates the influence of the application of more than one polymerisation regime on the analytical sensitivity of the sensors. Two polymerisation protocols were used: conventional galvanostatic and combined galvanostatic-potentiodynamic procedures. The total amount of the electricity and, consequently, the thickness of the polymer films in both cases were the same.

Galvanostatic and potentiodynamic procedures are carried out sequentially using the polymerisation solution concentrations and polymerisation cell format previously described in example 4. The electrochemical polymerisation was carried out using μAutolab II potentiostat-galvanostat (EcoChemie), galvanostatic current density was 0.1 mA/cm$^2$ for 150 s (15 mC/cm$^2$) followed by a single cyclic voltage scan with the scan rate 0.05 V/sec and a step potential of 2.44 mV. The lower boundary potential is −0.2 V. The upper boundary potential is 1.90 V (Procedure 1). Galvanostatic procedure was carried out with current density 0.1 mA/cm$^2$ for 300 s (Procedure 2), which gave approximately the same amount of electricity as in Procedure 1 (15 mC/cm$^2$). Other parameters were the same as for Procedure 1.

The resulting sensors were treated after the polymerisation as described in previous examples and their analytical sensitivity was tested accordingly as in Example 1 using two concentrations of biotinylated HRP (0 and 0.1 ng/ml). The results are in the table below.

| Applied procedure | Signal, mV | |
|---|---|---|
| | 0 ng/ml, [HRP-biotin] | 0.1 ng/ml, [HRP-biotin] |
| Procedure 1 | 14 | 51 |
| Procedure 2 | 11 | 23 |

This example demonstrates the influence of application of two polymerisation regimes. The potentiodynamic step can be 'imitated' by using more than one level of current in galvanosatic procedure (see previous and next examples).

The application of two or more regimes allows more strict control of the redox properties of the polymer film and consequently to tailor the analytical sensitivity of the sensors.

Example 6

Figure 5:
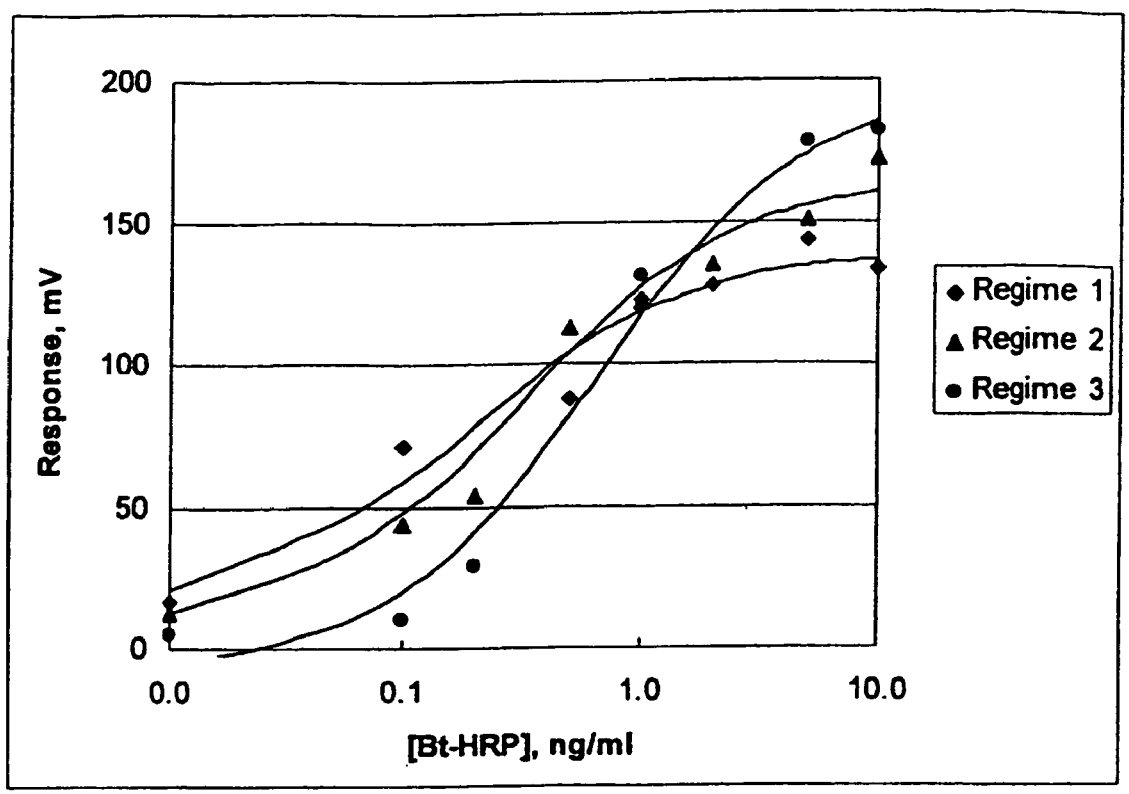
FIG. 5 illustrates the effect of various galvanostatic polypyrrole growth regimes on the response to biotinylated HRP (Bt-HRP). Each growth regime consists of a sequence of galvanostatically controlled current steps in which each step may be applied for a time between 10 to 1000 s.

This example demonstrates that by varying the parameters for the galvanostatic regime the electrochemical polymer deposition can be tailored to suit the requirements of a particular assay. In FIG. 5 "Regime 1" produces sensors with high "sensitivity" (0 to 0.1 ng/ml response) but low "dynamic" range (0 to 10 ng/ml response) Sensors produced using "Regime 3" have a much larger dynamic range but lower sensitivity. The electrochemical polymerisation was carried out using a μAutolab II (EcoChemie) computer controlled electrochemical measurement system. Forty electrodes of a circular design (diameter=1.5 mm) were placed in a linear cell parallel to a platinum auxiliary electrode. The cell was filled with the an aqueous solution containing pyrrole (7.5 mM) and SDS (0.17 mM). Polymer was deposited onto the electrodes using the galvanostatic regime in which a series of current steps are performed giving a total charge passed of between 13 to 24 mC/cm$^2$. After the electrochemcial polymer deposition had ended, the sensors were treated as described in previous examples and their analytical sensitivity determined using biotinylated HRP concentrations in the range 0 to 10 ng/ml.

Example 7

Figure 6:
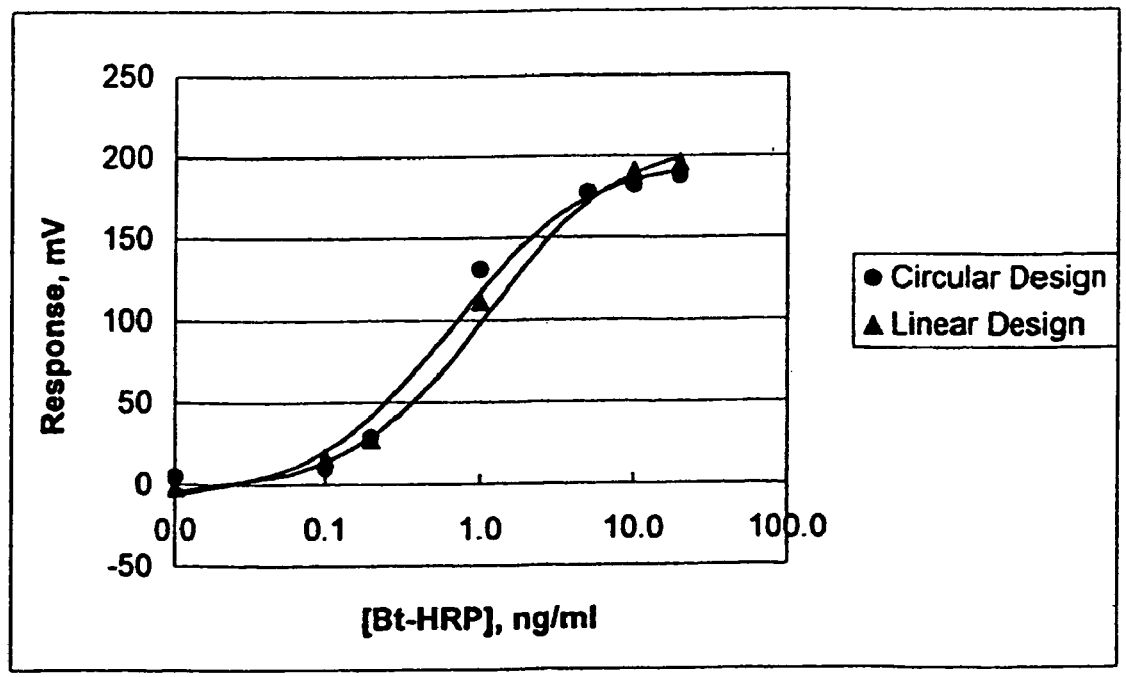
FIG. 6 illustrates the effect of the electrode design on the response to biotinylated HRP (Bt-HRP). The "linear" electrode design consists of an electrode design in which the width of the electrode is significantly less than the length of the electrode. The "circular" design consists of a circular or disc shaped electrode.

This example demonstrates that different shaped electrode designs produce sensors that respond slightly differently to the same levels of biotinylated HRP. In FIG. 6 a circular design (diameter=1.5 mm$^2$) is compared with a linear design (length=1 mm, width=0.25 mm). The circular electrode design produces a sensor which has a lower dynamic range and lower sensitivity than the linear design.

Both sensors were produced using the galvanostatic regime, with conditions as described in previous examples. The total current passed during polymer deposition was 24 mC/cm$^2$ for the circular electrode and 210 mC/cm$^2$ for the linear electrode type.

REFERENCES

The contents of the following documents are to be considered as incorporated into the present application by reference.
1. Ivaska A., Analytical application of conductive polymers. // Electroanalysis, 3 1991, 247-254.
2. Biosensors. Fundamentals and Application, Oxford, 1987.
3. Sadik O. A., Talaie A., Wallace G. G, Inherently conductive polymers—a versalite and adaptive chemical sensing system. // Journal Of Intelligent Material Systems And Structures, Vol. 4, 1993.

4. Ghindilis A., Atanasov A., Wilkins M., Wilkins E., Immunosensors: electrochemical sensing and other engineering approaches. // Biosensors & Bioelectronics, Vol. 13, No. 1, 113-131.
5. Michalska A., Ivaska A., Lewenstam A., Modelling potentiometric sensitivity of conductive polymer. // Analytical Chemistry, 69, 1997, 4060-4064.
6. Havas J., Ion- and Molecule-Selective Electrodes in Biological Systems, Budapest, 1985.
7. Adeloju S. B., Shaw S. J., Wallace G. G., Polypyrrole-based amperometric biosensor for sulphite determination. // Electroanalysis, 6, 1994.
8. Lu W., Zhou D., Wallace G. G., Enzymatic sensor based on conducting polymer coating on metallised membranes. // Analytical Communications, Vol. 35, 1998.
9. Michalska A., Hulanicki A., Lewenstam A., All solid-state hydrogen ion-selective electrode based on a conducting poly(pyrrole) solid contact. // Analyst, Vol. 119, 1994, 2417-2420.
10. Migdalski J., Blaz T., Lewenstam A., Conducting polymer-based ion-selective electrodes. // Analytica Chimica Acta, 322, 1996, 141-149.
11. Ghindilis A., Atanasov A., Wilkins E., Potentiometric immunoelectrode for fast assay based on direct electron transfer catalysed be peroxidase. // Sensors And Actuators, B34, 1996, 528-532.
12. Ghindilis A., Kurochkin I., Glucose potentiometric electrodes based on mediatorless bioelectrocatalysis. A new approach. // Biosensors & Bioelectronics, 9, 1994, 353-357.
13. Adeloju S. B., Shaw S. J., Wallace G. G., Polypyrrole-based potentiometric for urea. Part 1. Incorporation of urease. // Analytica Chimiva Acta, 281, 1993, 611-620.
14. Schasfoort R. B. M., Kooyman R. P. H., Bergveld P., Greve J., A new approach to immunoFET operation. // Biosensors and Bioelectronics, 5, 1990, 103-124.
15. Schasfoort R. B. M., Keldermans C. E. J. M., Kooyman R. P. H., Bergveld P., Greve J., Competitive immunological detection of progesterone by means of the ion-step induced response of an ImmunoFET. // Sensors and Actuators B1, 1990, 368-372.
16. John R., Spencer M., Wallace G. G., Smyth M. R., Development of a polypyrrole-based human serum albumin sensor. // Analytica Chimica Acta, 249, 1991, 381-385.
17. Riviello J. M., Wallace G. G., Sadik O. A., Method and apparatus for pulsed electrochemical detection using polymer electroactive electrodes. // U.S. Pat. No. 5,403,451, 1994.
18. Giuseppe-Elie A., Chemical and biological sensors having electroactive polymer thin film attached to microfabricated devices and processing immobilised indicator moieties. // U.S. Pat. No. 5,766,934, 1994.
19. Tarasevich M. R., Orlov S. B., Shkolnikov E. I, The electrochemistry of polymers, Moscow, 1990.
20. Laboratory Techniques in Electroanalytical Chemistry, New York, 1996.
21. Bard A. J., Faulkner L. R., Electrochemical Methods. Fundamentals and Application, New York, Chichester, Brisbane, Toronto, 1980.
22. Lewenstam A., Bobacka J., Ivaska A., Mechanism of ionic and redox sensitivity of p-type conducting polymers. Part 1. Theory. // Journal of Electroanalytical Chemistry, 368, 1994, 23-31.
23. Bobacka J., Gao Z., Ivaska A., Lewenstam A., Mechanism of ionic and redox sensitivity of p-type conducting polymers. Part 2. Experimental study of polypyrrole. // Journal of Electroanalytical Chemistry, 368, 1994, 33-41.
24. Michalska A., Lewenstam A., Ivaska A., Hulanicki A., Study of polypyrrole film as redox electrode. // Electroanalysis, 5, 1993, 261-263.
25. Michalska A., Lewenstam A., Potentiometric selectivity of p-doped polymer films. // Analytica Chimica Acta, 406, 2000, 159-169.
26. Bobacka J., Grzesczuk M., Ivaska A., Electron transfer at conducting polymer film electrodes: mechanism and kinetics of ferrocene oxidation at poly(3-octythiophene). // Journal Of Electroanalytical Chemistry, 427, 1997, 63-69.
27. Hulanicki A., Michalska A., Lewenstam A., Bifunctionality of chemical sensors based on the conducting polymer polypyrrole. // Talanta, Vol. 41, No. 2, 1994, 323-325.
28. Damaskin B., Petry O., Electrochemistry, Moscow, 1987.
29. Zhao H., Price W. E., Wallace G. G., Effect of counterion employed during synthesis on the properties of polypyrrole membranes. // Journal of Membrane Science, 87, 1994, 47-56.
30. Gao Z., Bobacka J., Lewenstam A., Ivaska A., Electrochemical behaviour of polypyrrole film polymerised in indigo carmine solution. // Electrochimica Acta, Vol. 39, No. 5, 1994, 755-762.
31. Gao Z., Bobacka J., Lewenstam A., Ivaska A., Electrochemical properties of polypyrrole films polymerised in the presence of Methylene Blue. // Synthetic Metals, 62, 1994, 117-123.
32. Adeloju S. B., Shaw S. J., Wallace G. G., Polypyrrole-based potentiometric biosensor for urea. Part 2. Analytical optimisation. // Analytica Chimica acta, 281, 1993, 621-627.
33. Taniguchi I., Yasukouchi K., Tsuji I., Fujiyasu T., Potential-causing membrane for immunosensor. // U.S. Pat. No. 4,839,017, 1987.
34. Wallace G. G., Lin Y. P., Preparation and application of conducting polymers containing chemically active counterions for analytical purposes. // Journal of Electroanalytical Chemistry, 247, 1988, 145-156.
35. Tatsuma T., Gondaira M., Watanabe T., Peroxidase-incorporated polypyrrole membrane electrodes. // Analytical Chemistry, 64, 1992, 1183-1187.
36. Sadik O. A., John M. J., Wallace G. G., Barnett D., Clarke C., Laing D. G., Pulsed amperometric detection of Thaumatin using antibody-containing poly(pyrrole) electrodes. // Analyst, Vol. 119, 1994.
37. Lu W., Zhao H., Wallace G. G., Pulsed electrochemical detection of proteins using conducting polymer based sensors. // Analytica Chimica Acta, 315, 1995, 27-32.
38. Lu W., Zhao H., Wallace G. G., Detection of cytochrome C using a conducting polymer mediator containing electrode. // Electroanalysis, 8, No. 3, 1996, 248-251.
39. Lu W., Nguyen T. A., Wallace G. G., Protein detection using conducting polymer microarrays. // Electroanalysis, 10, No. 16, 1998, 1101-1107.
40. Barisci J. N., Hughes D., Minett A., Wallace G. G., Characterisation and analytical use of a polypyrrole electrode containing anti-human serum albumin. // Analytica Chimica Acta, 371, 1998, 39-48.
41. Adelogu S. B., Moline A. N., Fabrication an ultra-thin polypyrrole-glucose oxidase film from supporting electrolyte-free monomer solution for potentiometric biosensing of glucose. // Biosensors & Bioelectronics, 16, 2001, 133-139.
42. Guiseppi-Elie A., Method of measuring an analyte by measuring electrical resistance of a polymer film reacting with the analyte. // U.S. Pat. No. 5,312,762, 1991.
43. Guiseppi-Elie A., Chemical and biological sensors having electroactive polymer thin films attached to microfabricated devices and possessing immobilised indicator moieties. // U.S. Pat. No. 5,766,934, 1994.
44. Lewenstam A., Matuszewski W., Trojanowicz M., Procedure and apparatus for the determination of concentration of ammonia, and a procedure for the manufacturing of a detector. // U.S. Pat. No. 5,498,323, 1994.
45. Partridge A. C., Harris. P. D., Andrews M. K., Deposition of thin electroconductive polymer film of desired resistance for gas sensing applications. // WO9811279A1, 1997.
46. Wallace G. G., Antibody containing electrode. // WO8911649, 1988.
47. Kasparov S. V., Farmakovsky D. A., Electrochemical immunoassay. // WO 96/02001, 1994.
48. Heiduschka P., Preschel M., Rosch M., Goprl W., Regeneration of an electropolymerised polypyrrole layer for the amperometric detection of ammonia. // Biosensors & Bioelectronics, Vol. 12, No. 12, 1997, 1227-1231.
49. Warriner K., Higson S., Christie I., Ashworth D., Vadgama P., Electrochemical characteristics of two model electropolymerised films for enzyme electrodes. // Biosensors & Bioelectronics, Vol. 11, No. 6/7, 1996, 615-623.
50. Farmakovski D. A., Milanovski E. Y., Cherkasov V. R., Biryukov Y. S., Komarov B. V., Method of electrochemical detection of immunoactive macromolecules. // WO 98/37409, 1998.
51. Farmakovski D. A., Milanovski E. Y., Cherkasov V. R., Biryukov Y. S., Leonardova O., Method of electrochemical analysis of an analyte. // International patent application number PCT/GB99/02785 filed 24 Aug. 1999, published as WO 00/11473, 2 March 2000.
52. Pei Q., Qian R., Protonation and deprotonation of polypyrrole chain in aqueous solutions. // Synthetic Metals, 45, 1991, 35-48.
53. Techniques of electrochemistry, New York, 1972.

The invention claimed is:

1. A method for producing highly sensitive potentiometric sensors by coating of electrically conductive electrodes with an electroconductive polymer, which method comprises the steps of:
  (a) preparing an aqueous solution for electrochemical polymerisation comprising monomeric units of the electroconductive polymer at a concentration in the range of 0.002-0.05M; and a supporting electrolyte, which also serves as a doping agent, at a concentration in the range of 0.0001-0.005M;
  (b) assembling an electrochemical polymerisation cell comprising the solution for electrochemical polymerisation, an auxiliary electrode, one or more working electrodes to be coated with electroconductive polymer, and optionally a reference electrode; and
  (c) coating the working electrode(s) with a polymer film by the electrochemical synthesis of polymer from the electrochemical polymerisation solution using at least one of the following electrochemical regimes:
    (i) applying a cyclic voltage in the range −0.2-+2.0 V vs Ag/AgCl reference electrode between the working electrode(s) to be coated and the auxiliary electrode;
    (ii) applying a constant current in the single or multiple current steps with given current density in a range 0.01-1 mA/cm$^2$ between working electrode(s) to be coated and auxiliary electrode for defined period of time such that final quantity of electricity passed through working electrode(s) will lie in a range 10-250 mC/cm$^2$;
    (iii) applying a constant potential in a single or multiple potential steps at the range 0-3 V between working electrode(s) to be coated and a reference electrode for defined period of time such that final quantity of electricity passed through the working electrode(s) will lie in a range 10-250 mC/cm$^2$.

2. A method according to claim 1 for producing highly sensitive potentiometric sensors by coating of electrically conductive electrodes with an electroconductive polymer, wherein in step (c) two or more current steps are applied in a galvanostatic regime.

3. A method according to claim 1 for producing highly sensitive potentiometric sensors by coating of electrically conductive electrodes with an electroconductive polymer, wherein in step (c) two or more potential steps are applied in a potentiostatic regime.

4. A method, according to claim 1 for producing highly sensitive potentiometric sensors by coating of electrically conductive electrodes with an electroconductive polymer, wherein in step (c) two or more polymerisation regimes, are applied.

5. A method, according to claim 4 for producing highly sensitive potentiometric sensors by coating of electrically conductive electrodes with an electroconductive polymer, wherein in step (c) the two or more polymerisation regimes are selected from the group consisting of galvanostatic, potentiodynamic, and potentiostatic regimes, are applied.

6. A method according to claim 1 wherein in regime (i) the cyclic electric potential is applied for 1-15 cycles.

7. A method according to claim 1 wherein in regime (ii) the number of applied current steps is 1-5.

8. A method according to claim 1 wherein in step (c) the electrochemical regimes (i), (ii), (iii) and (iv) are performed sequentially or in any combination to coat the electrode(s) with a polymer film by the electrochemical synthesis of polymer from the electrochemical polymerisation solution.

9. A method according to claim 8 wherein step (c) comprises performing electrochemical regimes (i) and (ii) or (ii) and (iii) sequentially.

10. A method according to claim 1 wherein the ratio between concentrations of monomeric units of the electroconductive polymer and supporting electrolyte in the electrochemical polymerisation solution is in the range 2:1 to 30.

11. A method according to claim 10 wherein the ratio between concentrations of monomeric units of the electroconductive polymer and supporting electrolyte in the electrochemical polymerisation solution is approximately 25:1.

12. A method according to claim 10 wherein the ratio between concentrations of monomeric units of the electroconductive polymer and supporting electrolyte in the electrochemical polymerisation solution is in the range 5:1 to 30:1.

13. A method according to claim 1 wherein the monomeric units of the electroconductive polymer are pyrrole, thiophene, furan or any mixture thereof.

14. A method according to claim 1 wherein sodium dodecylsulphate is used as the supporting electrolyte.

15. A method according to claim 1 for use in production of two or more highly sensitive potentiometric sensors in a single polymerisation reaction, wherein in the cell for electrochemical polymerisation of step (b) two or more electrodes to be coated are combined in one unit having one common electrical contact.

16. A method according to claim 15 wherein all electrodes to be coated in potentiodynamic or potentiostatic regimes are positioned equidistant from the auxiliary electrode.

17. A method according to claim 15 wherein all electrodes to be coated are positioned preferably equidistant from the reference electrode.

18. A method according to claim 1, which comprises the additional steps of:
(d) washing the electroconductive polymer coated electrode(s) obtained in step (c) in deionized water; and
(e) removing unbound water from the electroconductive polymer layer.

19. A method according to claim 18 wherein in step (d) the electroconductive polymer coated electrode(s) are washed with deionized water until traces of monomeric units of the electroconductive polymer and supporting electrolyte are no longer detectable.

20. A method according to claim 18 wherein in step (e) the unbound water is removed from the electroconductive polymer layer by heating the electrode(s) in an incubator for at least 8 hours.

21. A method according to claim 20 wherein the temperature of heating is within range 25-50° C., preferably 30-40° C.

22. A method according to claim 18 wherein in step (e) the unbound water is removed from the electroconductive polymer layer by lyophilization.

* * * * *